US012642575B2

(12) United States Patent
Franke et al.

(10) Patent No.: US 12,642,575 B2
(45) Date of Patent: *Jun. 2, 2026

(54) SYSTEM AND METHODS FOR MINIMALLY INVASIVE ABLATION WITH INJECTABLE WIRE STRUCTURE DEVICES

(71) Applicant: NEURONOFF, INC., Cleveland, OH (US)

(72) Inventors: Manfred Franke, Cleveland, OH (US); Stephan Nieuwoudt, Cleveland, OH (US); David Bolus, Cleveland, OH (US); Derrick Liu, Cleveland, OH (US); Emily Szabo, Cleveland, OH (US); Shaher Ahmad, Cleveland, OH (US); Aniruddha Upadhye, Cleveland, OH (US); Sean Zuckerman, Cleveland, OH (US); Craig Watson, Cleveland, OH (US); Amelia Howe, Cleveland, OH (US); Morgan McGaughey, Cleveland, OH (US); Victoria Miduri, Cleveland, OH (US)

( * ) Notice: Subject to any disclaimer, the term of this patent is extended or adjusted under 35 U.S.C. 154(b) by 241 days.

This patent is subject to a terminal disclaimer.

(21) Appl. No.: 18/285,349

(22) PCT Filed: Mar. 16, 2022

(86) PCT No.: PCT/US2022/020652
§ 371 (c)(1),
(2) Date: Oct. 2, 2023

(87) PCT Pub. No.: WO2022/212064
PCT Pub. Date: Oct. 6, 2022

(65) Prior Publication Data
US 2024/0216040 A1 Jul. 4, 2024

Related U.S. Application Data

(63) Continuation-in-part of application No. 18/278,160, filed as application No. PCT/US2021/033007 on May
(Continued)

(51) Int. Cl.
*A61B 18/14* (2006.01)
*A61B 18/18* (2006.01)
(Continued)

(52) U.S. Cl.
CPC .......... *A61B 18/14* (2013.01); *A61B 18/1815* (2013.01); *A61B 90/39* (2016.02);
(Continued)

(58) Field of Classification Search
CPC . A61B 18/14; A61B 18/1477; A61B 18/1492; A61B 18/1815;
(Continued)

(56) References Cited

U.S. PATENT DOCUMENTS 5,122,136 A * 6/1992 Guglielmi ........ A61B 17/12145
606/41
6,979,330 B2 * 12/2005 Kelly ...................... A61N 1/06
606/41
(Continued)

*Primary Examiner* — Michael F Peffley
(74) *Attorney, Agent, or Firm* — Joel Douglas; Thomas Ciesco

(57) ABSTRACT

A chronic and/or acute system and methods of minimally invasive ablation with wire structure devices dispensed through a needle without open cut downs or laparoscopy and using energy forms including radiofrequency, microwave and direct current.

20 Claims, 35 Drawing Sheets

Related U.S. Application Data 18, 2021, application No. 18/285,349 is a continuation-in-part of application No. 18/026,705, filed as application No. PCT/US2021/033265 on May 19, 2021.

(60) Provisional application No. 63/167,836, filed on Mar. 30, 2021, provisional application No. 63/171,780, filed on Apr. 7, 2021, provisional application No. 63/184,656, filed on May 5, 2021, provisional application No. 63/306,896, filed on Feb. 4, 2022.

(51) Int. Cl.
    *A61B 90/00*        (2016.01)
    *A61B 18/00*        (2006.01)

(52) U.S. Cl.
    CPC ............... *A61B 2018/00434* (2013.01); *A61B 2018/00577* (2013.01); *A61B 2018/00613* (2013.01); *A61B 2018/0072* (2013.01); *A61B 2018/1437* (2013.01); *A61B 2018/144* (2013.01); *A61B 2018/1869* (2013.01); *A61B 2090/3966* (2016.02); *A61B 2218/002* (2013.01)

(58) Field of Classification Search
    CPC .......... A61B 2018/00434; A61B 2018/00577; A61B 2018/00613; A61B 2018/0072; A61B 2018/1425; A61B 2018/1437; A61B 2018/144; A61B 2018/1869; A61B 2090/3966; A61B 2218/002; A61B 90/39
    See application file for complete search history.

(56)                References Cited

U.S. PATENT DOCUMENTS

| | | | |
|---|---|---|---|
| 2006/0041277 A1* | 2/2006 | Deem ................ | A61N 1/36117 607/3 |
| 2007/0282407 A1* | 12/2007 | Demarais ................. | A61N 7/02 607/113 |
| 2012/0136349 A1* | 5/2012 | Hastings ............ | A61B 18/1492 606/34 |
| 2013/0238066 A1* | 9/2013 | Boggs, II ............. | A61N 1/0456 607/116 |
| 2019/0374277 A1* | 12/2019 | Bagwell ............. | A61B 18/1492 |

* cited by examiner

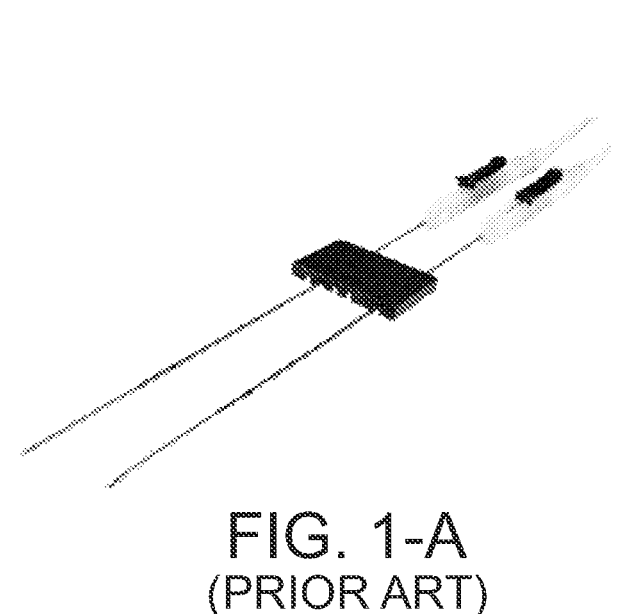
FIG. 1-A
(PRIOR ART)
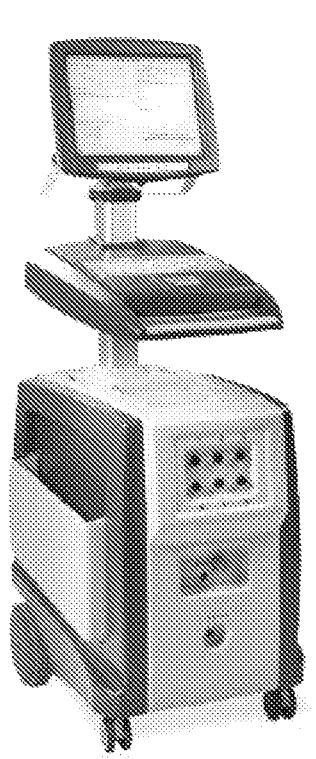
FIG. 1-B
(PRIOR ART)

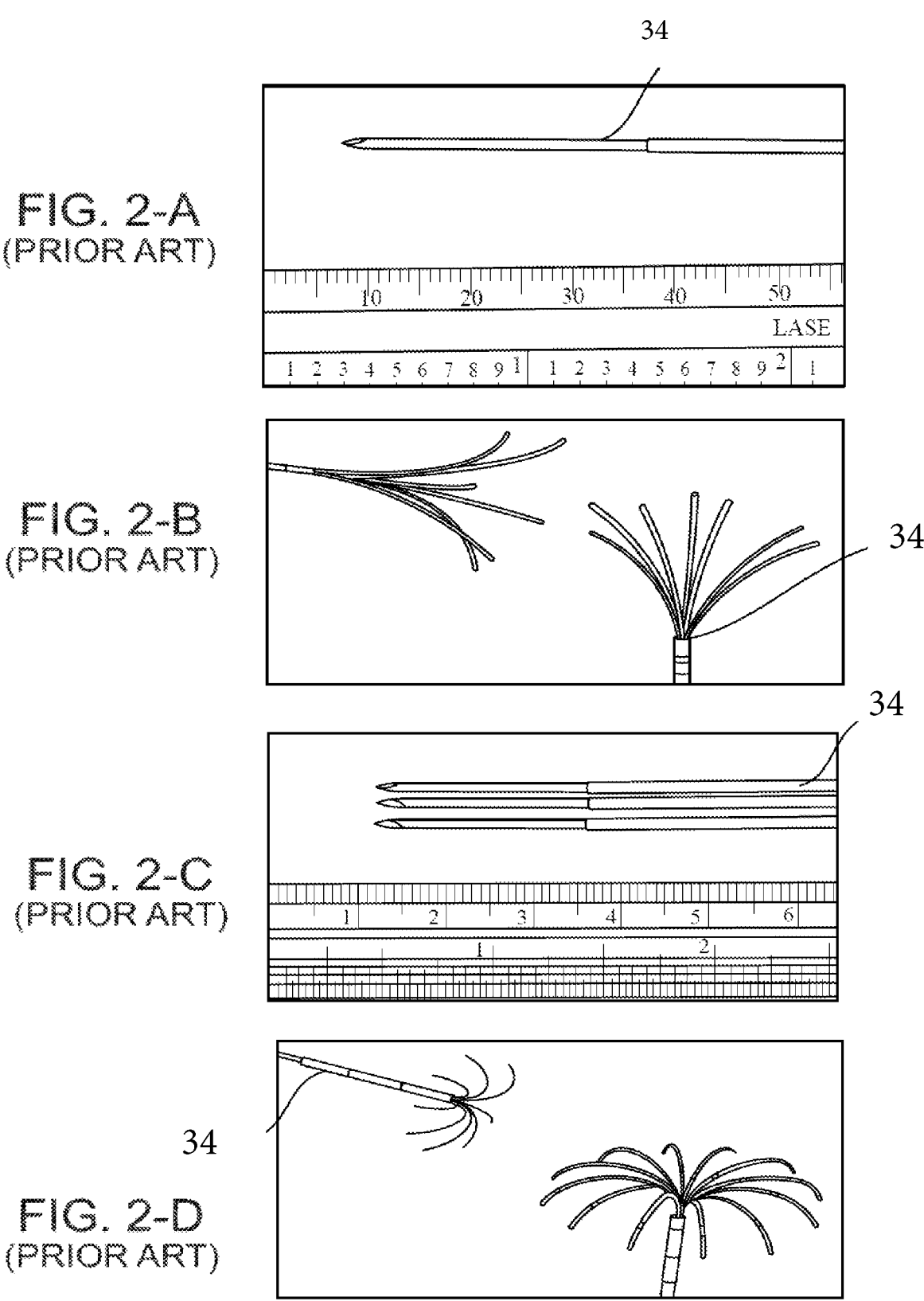
FIG. 2-A
(PRIOR ART)
FIG. 2-B
(PRIOR ART)
FIG. 2-C
(PRIOR ART)
FIG. 2-D
(PRIOR ART)

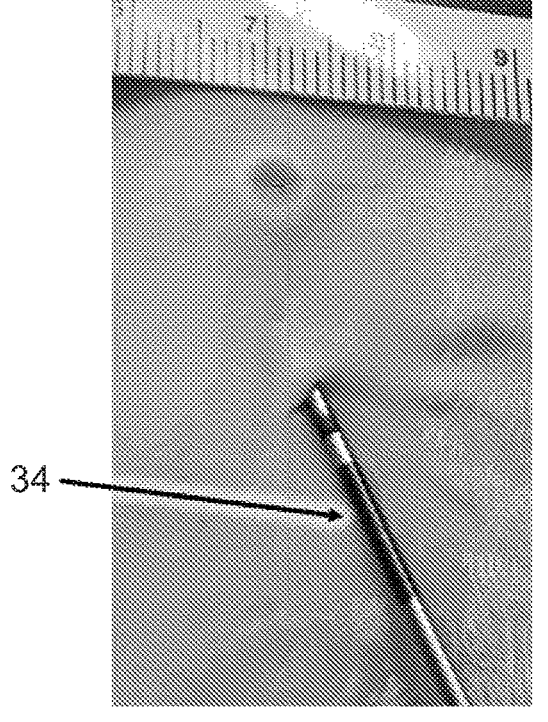
FIG. 3-A
(PRIOR ART)
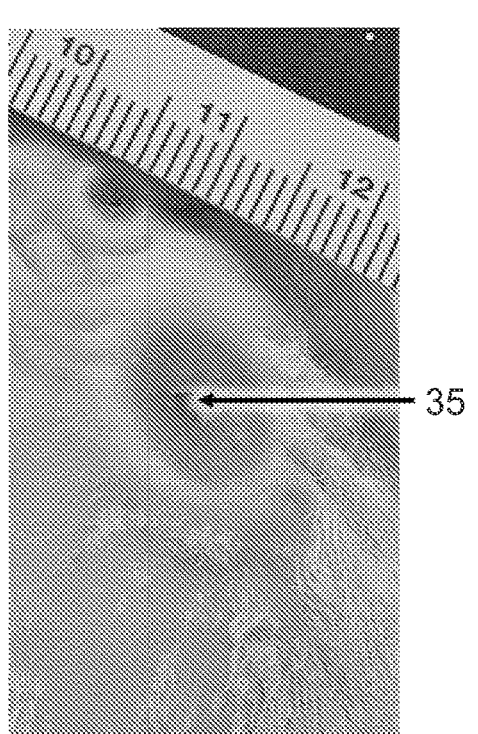
FIG. 3-B

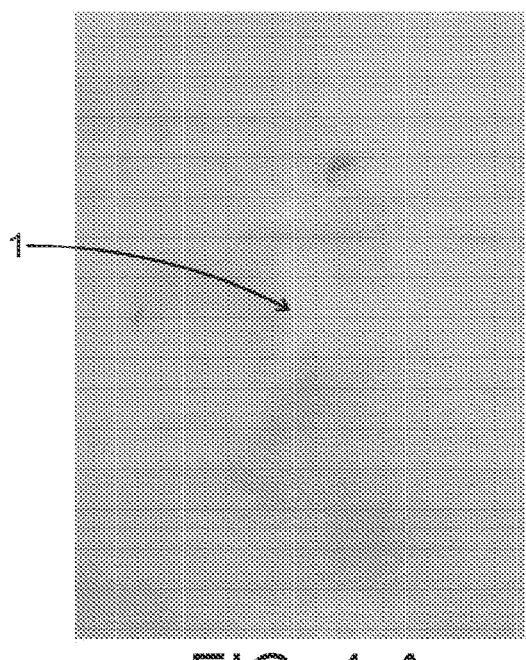
1
FIG. 4-A
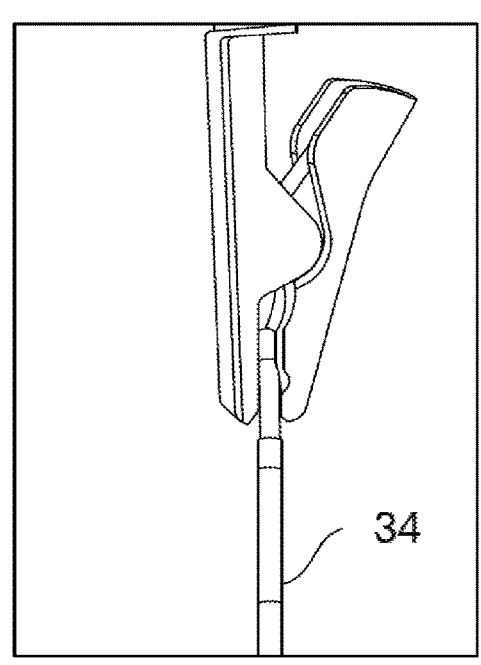
34
FIG. 4-B
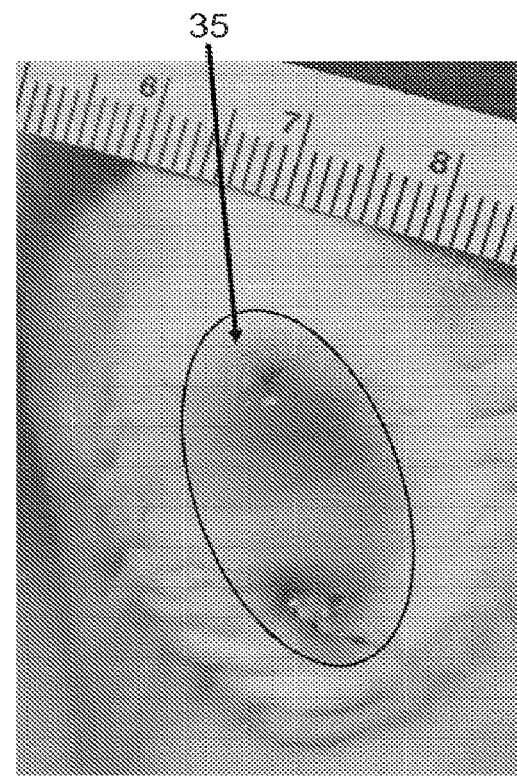
35
FIG. 4-C

36
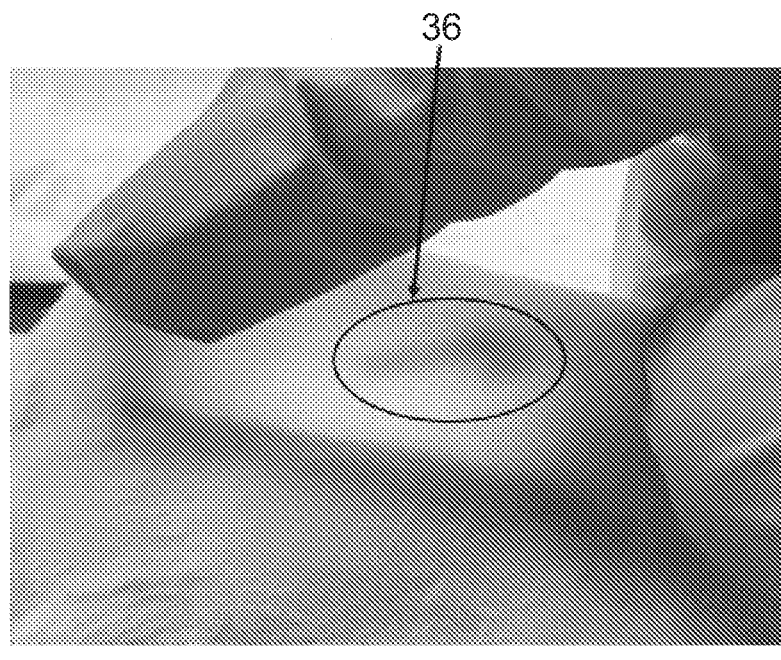
FIG. 7-A
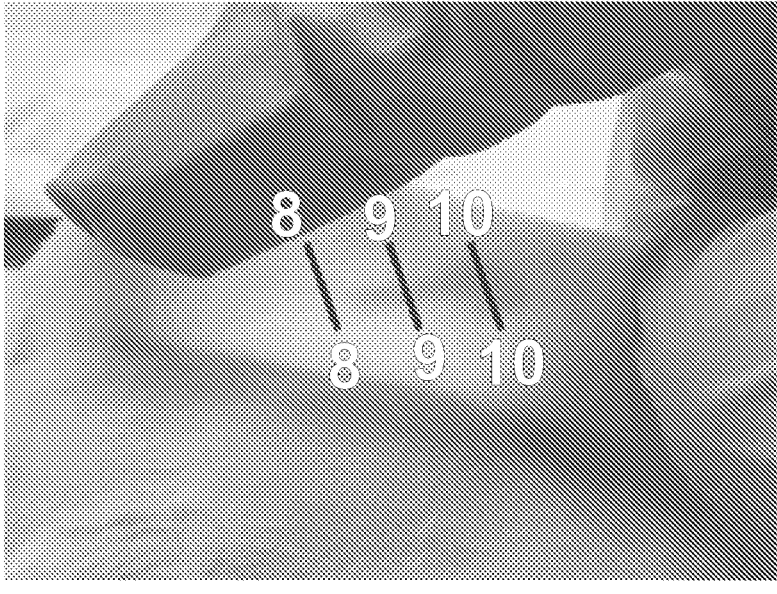
FIG. 7-B

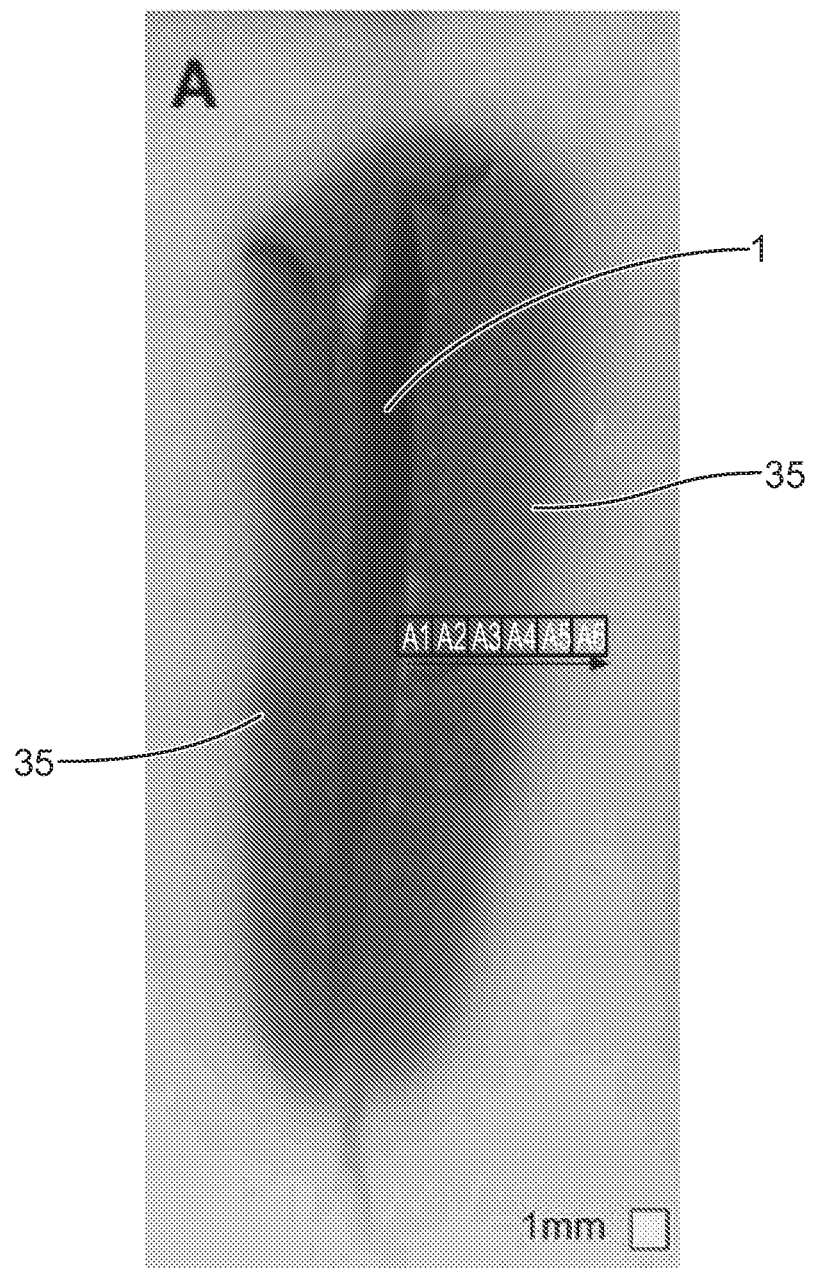
FIG. 18-A

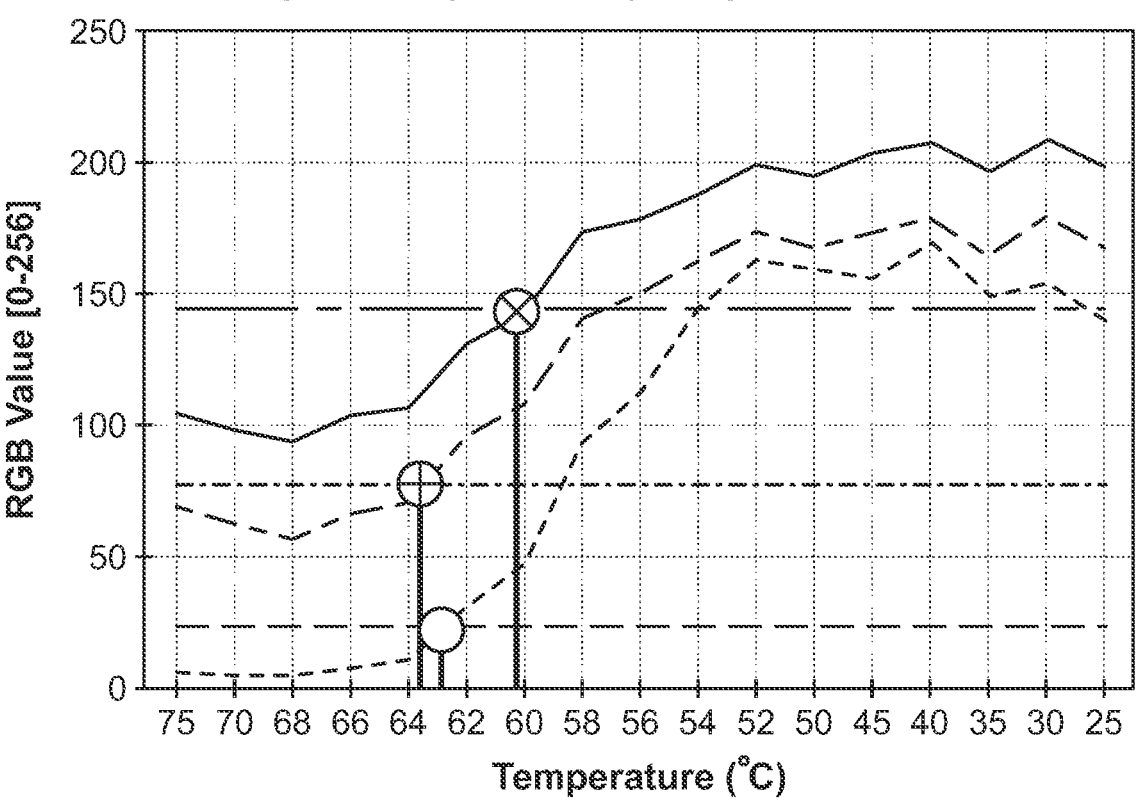
FIG. 18-B

A1-A5 Temperature Estimate vs. Distance
(Radial)

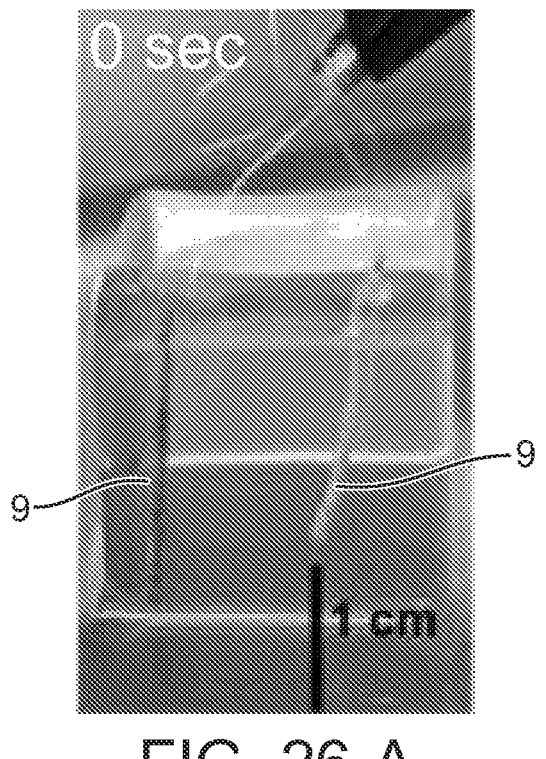
FIG. 26-A
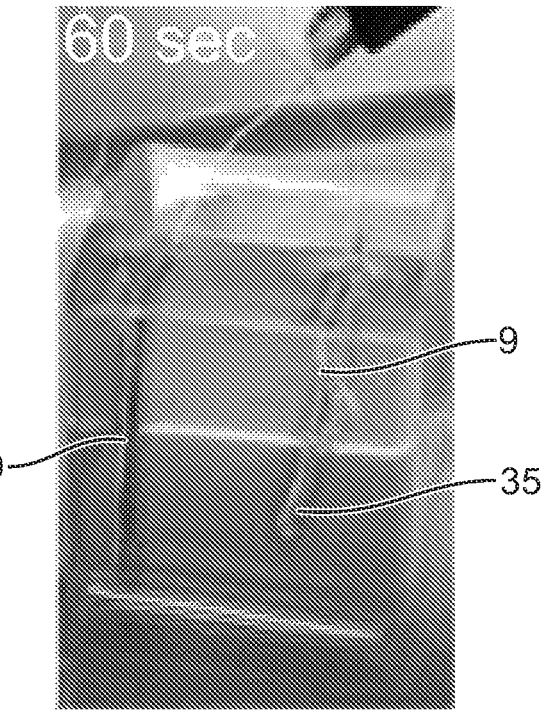
FIG. 26-B
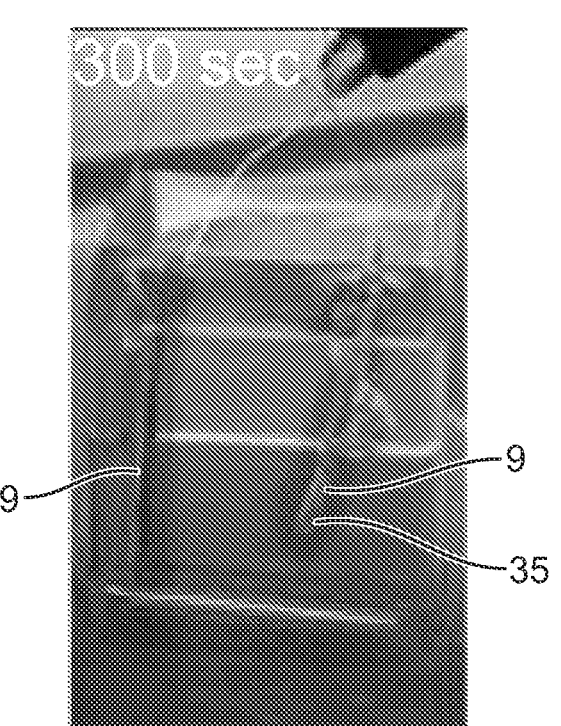
FIG. 26-C
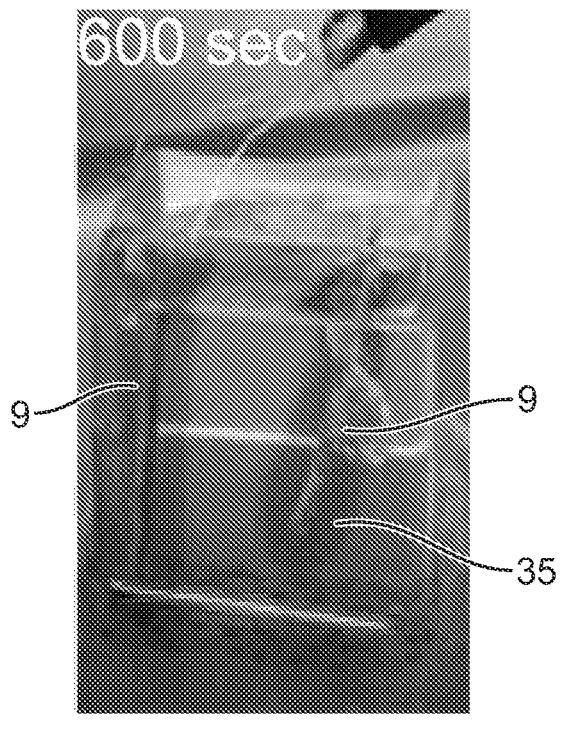
FIG. 26-D

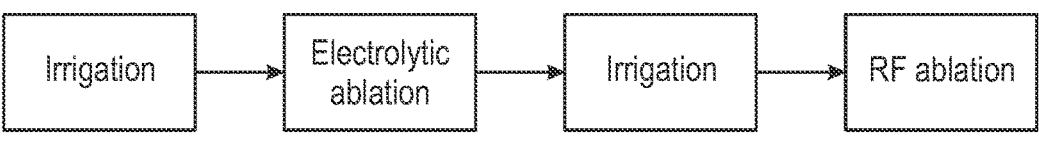

FIG. 38

```
┌──────────────────────┐
│  Determine location of│
│  desired / target lesion│
│      via imaging      │
└──────────────────────┘
            │
            ▼
┌──────────────────────┐
│    Deploy initial     │
│  volume of Device via │
│  needle into or around│
│     target tissue     │
└──────────────────────┘
            │
            ▼
┌──────────────────────┐
│  Apply RFA + irrigation│
│    via Device for some │
│    time (temperature or│
│   impedance endpoint) │
└──────────────────────┘
            │
            ▼
```

┌──────────────────┐   Excess    ┌──────────────────────┐  Insufficient  ┌──────────────────┐
│     Retract      │   Volume    │  Assess qualilty / ablation│  Volume    │  Deploy more     │
│  Device into     │◄────────────│  sufficiency via imaging│───────────►│  Device via      │
│deployment needle,│             │  (untrasound, CT, MRI) +│            │  needle, verify  │
│  verify position │             │    addition contrast  │            │    position      │
└──────────────────┘             └──────────────────────┘            └──────────────────┘
                                            │
                                            ▼
                                 ┌──────────────────────┐
                                 │  Retract and remove   │
                                 │  Device from target   │
                                 │    tissue (Acute)     │
                                 └──────────────────────┘

FIG. 39

SYSTEM AND METHODS FOR MINIMALLY INVASIVE ABLATION WITH INJECTABLE WIRE STRUCTURE DEVICES

STATEMENT REGARDING RELATED APPLICATIONS

This application claims priority to, and the full benefit of, U.S. provisional application No. 63/167,836 filed Mar. 30, 2021; U.S. provisional application No. 63/171,780 filed on Apr. 7, 2021; U.S. provisional application No. 63/184,656 filed on May 5, 2021; U.S. application Ser. No. 18/278,160, which is a National Phase entry of international application PCT/US21/33007 filed on May 18, 2021, U.S. application Ser. No. 18/026,705, which is a National Phase entry of international application PCT/US21/33265; and U.S. provisional application 63/306,896 filed on Feb. 4, 2022. This application also incorporates in their entirety international application PCT/US20/61374 filed on Nov. 19, 2020 (PCT '374) and international application #PCT/US20/33007 filed on May 18, 2021 (PCT '007), as if each were set forth herein.

FIELD OF THE INVENTION

The field is directed to the minimally invasive ablation of tissue with injectable devices comprising flexible wire structures.

BRIEF DESCRIPTION OF THE FIGURES

Note: This application adopts the reference numbers from PCT '007 in the following figures filed in this application.

FIG. 1-A is an image of a current electroporation probe and FIG. 1-B is an image of the companion generator, Nanoknife, by AngioDynamics.

FIG. 2 contains four images of existing devices in today's market. FIG. 2-A is an image of a 3 cm Single Active-Tip (Covidien Cool-Tip™). FIG. 2-B is a StarBurst® Expandable Electrode (Angiodynamics). FIG. 2-C is a Cluster Tri-Electrode 2.5 cm Active Tip (Covidien Cool-Tip™). FIG. 2-D is a LeVeen™ Expandable Anchor Electrode (Boston Scientific).

FIG. 3-A is an image of cadaver tissue with the end of a currently known RF ablation probe inserted to a subcutaneous point in the tissue to be ablated. FIG. 3-B is an image of the same cadaver tissue after ablation and removal of the probe and showing the pattern of ablation is limited to near the end of the probe.

FIG. 4-A is an image of cadaver tissue with a wire structure device implanted subcutaneously prior to RF ablation. FIG. 4-B shows the end of a gold wire in the wire structure device excised and clamped directly to an RF probe. FIG. 4-C is an image of the ablation pattern 35 in the cadaver tissue from the wire structure device.

FIG. 7-A is transdermal imaging of a subcutaneously implanted gold wire rope structure device in a J-hook shape, and FIG. 7-B is the same image with cross sections 8-8, 9-9 and 10-10 labeled.

FIG. 18 addresses post-experiment image-based temperature estimation in application of RF energy. FIG. 18-A is an image of an ablative zone effected by a 2 cm-length helical wire rope structure device subjected to 40 W power over minutes. Temperature zones A1-A6 are reported in FIG. 18-C. FIG. 18-B shows temperature estimation based on RGB value found 2 mm from device site compared to RGB value of control set across 25-70 degrees Celsius. FIG. 18-C shows temperature estimation vs. distance at zones 1-5 mm from the center of the ablative zone.

FIG. 19-A shows linear electrode placement, radial heat dispersion for a small (<3 cm) tumor, and complete ablation, and 19-B, 19-C and 19-D show multiple zones needed for larger targets such as some tumors.

FIG. 26-A, FIG. 26-B, FIG. 26-C and FIG. 26-D are images of two linear helical wire rope structures at similar scale coupled to the negative terminal of a DC power supply for 0, 60, 300 and 600 seconds, respectively, embedded into a tissue mimicking PAG phantom laced with a pH indicator.

FIG. 35 presents data from electrolytic ablation with a helical wire rope structure in a normo-ionic environment through stainless steel needle electrodes placed into pH-sensitive tissue mimicking phantom compared to a hyper-ionic environment over the same time and conditions.

FIG. 38 is a block diagram showing the progression for enhancing electrolytic ablation through irrigation.

FIG. 39 depicts steps in a method for enhancing RF ablation efficacy and reducing treatment time.

ASPECTS OF THE INVENTION

Figure 5:
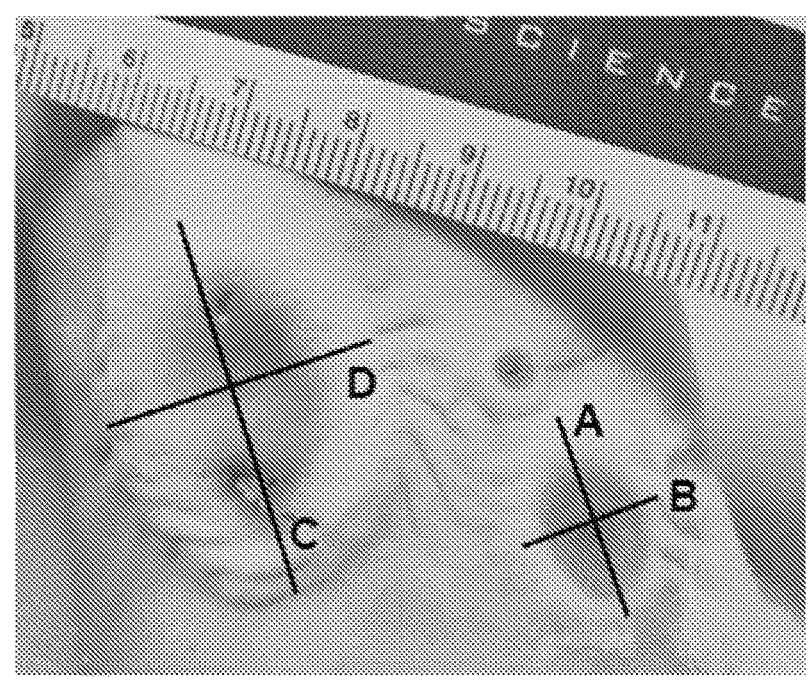
FIG. 5 is a photo showing a comparison of ablation patterns from the existing device in FIG. 3-B (one the right) and the larger one from a wire structure device on the right in FIG. 4-C for the same duration and same amount of RF energy.

As used herein, "wire structure" and "wire structure device" are umbrella terms including devices disclosed both in PCT '374 (non-helical wire structures) and in PCT '007 (helical wire rope structures).

Wire structure devices provide tools to solve inadequacies with prior systems and methods of ablating a tissue target such as a tumor or a peripheral nerve.

Many current methods of ablation rely upon the percutaneous insertion of probes to the tissue target so that energy conducted through the probes contacts the target directly to generate heat and destroy the tissue. Those methods are limited by the fact that probes may be relatively narrow to be inserted through the skin, in acute procedures, but their narrowness limits the size and configuration of the ablation pattern. Typical existing probes are straight, and even probes with semi-flexing components are limited by their lack of customizable extension "around corners" to hard-to-reach locations such as around a blood vessel.

The system and methods are configured for ablating a tissue target such as, hyper-thermally and/or non-thermally with an array of wire structure devices including those which are non-helical (rolled, folded, extruded, twisted, braided as in PCT '374) which are mechanically compliant when injected against or into bodily tissue, or using a helical wire rope structure device (PCT '007) that is less mechanically compliant but able to form a bunching anchor 8 when injected against, around, onto, or into biological tissue. Examples of the non-helical structure are shown in FIGS. 4-C, 8-10, and 29-30, and examples of the helical structure are in FIGS. 11-15, 18-A, 20, 22-28.

A flexible multi-stranded helical wire rope structure 1 of materials is configured to display desirable thermal conductivity, electrical conductivity, and heat capacity, making the device suitable for efficient electrical coupling, heat transfer, or electric field distribution. The manufacturing of a helical wire rope structure device outside the body may involve steps of rolling and/or folding. In an embodiment, one or more strand diameters in the wire structure may range from about 25 microns to about 75 microns, although in other embodiments strands outside this range are appropriate. Incorporating strands of greater thicknesses is a method of mechanical optimization for increasing rigidity of the helical coil or creating permanent curvatures at one or more points along the length of the wire structure upon deployment.

The system and methods can be placed chronically or acutely, or a combination of both. Tissue targets for ablation include without limitation tumors of the liver, kidney, lung, and bone, as well as peripheral nerves, as discussed further herein. The present method employs devices comprising thin, highly conductive wires and may be loaded and deployed into or surrounding a target tissue region through a straight or nonlinear dispenser of a predetermined length and diameter. The wire structure is capable of tissue ablation and repeated ablation through a number of energy modalities, including radiofrequency ablation (RF), direct current ablation (DC), microwave ablation (MW), or high intensity focused ultrasound (HIFU). The system is configured to enhance direct current (electrolytic) efficacy and reduces treatment time through increased locoregional cell permeability by (mild-HT, IRE) and increases diffusion of electrolytic product species into target volumes.

As shown in the figures herein, and described further in greater detail in PCT '007, the helical wire rope structure comprises coils of a wire rope comprising strands of fine wire which are not glued or cemented together, and the coils of wire rope enclose a hollow core exposed to bodily fluid. At least some of the coils are not coated with a stabilizer/insulator. As a result of this composition, many of the strands in the areas of non-coating are exposed to bodily fluids, and portions of the strands in the areas of coating bordering the areas of non-coating. The total surface area of the helical wire rope structure exposed to bodily fluid therefore exceeds the surface area of the strands in coils which are not coated. For example, for a helical wire rope structure having 3 centimeters not coated near the target tissue, composed of one hundred 25-micron strands wound around a 0.25 mm core, the total exposed/geometric surface area is 135 mm$^2$ per cm length. By comparison, the surface area for a typical 3 cm currently known ablation electrode can be within a range of approximately 108-122 mm$^2$, approximately 3 times smaller than the wire structure devices of the present system. The much larger surface area of the system lowers impedance and therefore increases charge injection capacity.

One aspect of the improved solution herein is to use implanted wire structure devices positioned at, on or in the tissue target, so that energy conducted through probes passes to the implanted devices which then progresses to the tissue target, where the greater resistance of the tissue creates heat for ablation. The helical and non-helical devices are flexible, bendable, stretchable, with the helical more so than the non-helical. The helical wire rope structure can take almost any shape, and as such these devices are configured to create larger and more complicated ablation patterns. The helical may create treatment patterns around corners created by essential structures such as blood vessels and peripheral nerves which are not treatment targets. With these devices being chronically implantable, this solution also allows repeated procedures using thinner probes or other techniques so that entry wounds caused by known probes are reduced, thereby producing less collateral damage and infection risk to healthy tissue of persons such as cancer patients who are often immunocompromised by chemotherapies and pharmaceuticals. More accurate and complete ablation can make the administration of chemotherapy more effective at lower concentrations as a result of increasing the permeability of tumor cell membranes which have been subject to ablation but not yet destroyed.

The wire structure devices of PCT '374 (non-helical wire structure devices) and PCT '007 (helical wire rope structures) have similarities. They may comprise fine wire and are injectable through a dispenser (e.g., a needle) in a minimally invasive procedure without an open cut down or even laparoscopy. They can be injected in a linear fashion when the needle is being retracted to form a linear path (or curved out of a curved needle). In varying degrees one or more may bend, flex and fold and integrate well with the tissue and offer large surface area to provide ample interface for energy exchange.

Amplitude and gradient of a generated field depends on the applied voltage and the distance between the devices. The tailored delivery of the highly conductive helical wire rope structure allows the user to introduce devices in a close arrangement to either irreversibly or temporarily electroporate tissue. Helical wire rope structures are also not restricted to fixed geometries, again, making it simple to ensure that the target is entirely enclosed within an applied field. Grounding can be achieved either by a separate internal or external device, or by use of two or more electrically charged delivery devices. The delivery devices herein may be nonmetallic to prevent interference with visualization techniques.

Differences between helical wire rope structure devices and non-helical wire structures allow them to be used by the clinician for different applications in ablation and other energy transfer therapies. The helical wire rope structure is configured to self-anchor during the placement procedure, unlike non-helical. This may not increase the wire density in that location, but instead may increase the cavity volume and thus target area for needle interfacing or volume of cavity that electrical energy may be deployed from into the tissue for stimulation or ablation applications. Non-helical does not bend as easily around a corner or fill and widen the cavity in a way that helical will. Non-helical is more compressible than helical. Wire to air (compaction) inside the needle (prior to deployment) is around 60 to 70% for helical whereas the wire to air ratio inside the needle for non-helical is about 20 to 30%. Helical is mechanically stronger against deformation from outside forces and will tend to bend over instead of compressing during normal body movements (not so during removal). Helical will not compress when ejected from a needle against mechanical pressure (such as when the dispenser is stationary) and will form a bunching anchor, but non-helical will compress when ejected from a needle. Helical can help to widen a cavity during the injection, but non-helical will instead compress in on itself, making it ideal around delicate structures. Non-helical can compress more in one or more predetermined locations during the placement to concentrate wire there for either increasing charge injection or easing the interfacing by having a more densely packed non-helical in one or more predetermined locations. Helical can be unzipped coil-by-coil for easy removal even after tissue in-growth but non-helical does not unzip and is less easily removed in a chronic stage with tissue in-growth. Both are easily removed if still in linear shape on injection day, meaning non-helical may compress but can still be pulled out before tissue in-growth, and helical may be removed via an unzipping of the coils even if it has self-formed an anchor.

The helical wire rope structure, loaded into a needle (linear or curved passive introducer) or flexible catheter (steerable, active introducer), is capable of deployment via the use of a bendable plunger, sufficiently dense hydrogel, or similar methods of pushing the coil within the needle. Insertion of the needle or flexible catheter may create a void in soft tissue by displacement. Bodily fluid (e.g., blood) ingress into the void is a natural consequence of the insertion of a device, and may be accompanied by the introduction of saline or a hydrogel, or gaseous microbubbles in the context of contrast-enhanced ultrasound. The helical wire rope structure inside the needle or flexible catheter may be combined with liquid, gel, gas, or a mixture of the three, to pass around or through crevices between the helix and the wall of the introducer, or through the centerline of the helix itself. As discussed elsewhere herein, hypertonic saline 43 injection in the context of ablation increases ionicity and conduction within the tumor, thereby increasing ablative volumes while preventing tissue desiccation that would otherwise limit ablation volume.

Both hyperthermic and non-thermal ablation modes may utilize high spatial targeting accuracy. Balancing the desire to apply irreversible damage to a whole tumor with reduction of harm to surrounding structures may be based on predictability. A variety of models exist which seek to mimic properties of biological tissue as simple, highly reproducible methods of evaluating device performance and creating therapy protocols, thereby eliminating the use of animal and human subjects. Ex vivo tissues are a common method of assessing a treatment volume. However, the heterogeneous nature of ex vivo tissue makes reproducible characterization difficult. Assessments of ablation using ex-vivo tissues may utilize cutting, staining, and subjective observation of tissue. Other efforts have focused on the creation of tissue-mimicking phantoms for quantitative and predictive measures of device performance. In evaluating hyperthermic ablation modes, proposed formulations have used agarose and polyacrylamide gels (PAGs) incorporated with heat-sensitive materials such as bovine serum albumin and thermochromic compounds (liquid crystals, leuco dyes, or permanent color change inks). Gels such as agarose and PAG have desirable properties, including melting points higher than those achieved through ablation, and the ability to be doped with materials to mimic properties such as electrical and thermal conductivity. The use of PAGs altered with sodium chloride and permanent color changing dyes allows for visualization and quantitative assessment of heat-affected zones caused by a device. The use of PAGs altered with pH indicators (i.e. phenol red) allows for visualization and quantitative assessment of locoregional pH changes surrounding a device. Temperatures as well as acidity may be backtraced through post-experimental image analyses and verified through the placement of thermocouples, fiber-optic thermometers, or micro-pH electrodes. This allows for the creation of models that predict temperature or pH change in response to supplied power for specific amounts of time, aiding in therapeutic planning for both thermal (RF ablation, MW, HIFU) and non-thermal (RE, IRE, EA) modes of ablation.

In one embodiment of the acute configuration, the system comprises a helical wire rope structure 1 integrated within the delivery needle (e.g., 18 or 20 gauge) and ablation probe. In the chronic configuration, the helical wire rope structure is transiently mechanically connected to the delivery probe and released after the placement and acute procedure to be left chronically. The chronically placed helical wire rope structure may then be re-interfaced. The irrigants may include a wide range of conductive fluids capable of dispersion through target tissue and device alike, as enabled by the hollow core 5 of the helical wire rope structure. Ablation methods herein include intermittent or constant delivery of an irrigant to a desired site, combined with techniques to generate lesioning via focal hyperthermia (e.g., RF) or induced changes in extracellular pH (e.g., DC/EA).

Methods which use thermal energy (e.g. through radiofrequency currents, microwaves, ultrasound, etc.) to destroy selectively undesirable tissue in the body have been applied frequently towards tumor eradication, nerve ablation for pain reduction, and many other medical applications. In the case of radiofrequency ablation, one or multiple devices are inserted into or adjacent to undesirable tissue, where passage of rapidly alternating current between devices or between device and a distal grounding pad induces frictional heat, and subsequently, local coagulative necrosis surrounding the source (device). The heat generated by the device propagates through the tissue by thermal conduction. A major limitation of this technique occurs with rapid, excessive temperature rise near the device (>100° C.). The consequence of this is tissue desiccation, where dried out tissue selectively adheres to the device surface to form an insulative layer, increasing impedances and preventing thermal energy conduction beyond a small range.

To address these limitations, methods for saline and other fluid enhanced ablation therapies (e.g, SERF™, StarBurst) have been applied to produce larger effective treatment zone sizes relative to conventional technique. For thermal ablation, these fluids have been shown to reduce desiccation of tissue at the surface of an active device and serve to distribute heat more evenly and thoroughly in surrounding tissue. For EA, such fluids increase the effective conductive surface area of the anode and cathode, enhancing the rate, total charge delivered, and extent or volume distribution of electrolysis products through surrounding tissue.

Previous irrigated-ablation methods have typically relied on fluid application through internal lumens/pores embedded within rigid devices to produce larger volume spherical ablation zones. The wire structures herein (helical and non-helical) are porous in the noncoated areas and is a flexible body, not rigid, in which the strands are configured to move in relation to one another. Their strands are not glued or bonded together, and therefore fluid is dispensed more readily throughout the entire length of the device into the target area of ablation than it could be dispensed through a single port on currently known ablation devices. The ablation zones generated by existing devices, even when enhanced by internal cooling or external irrigation, remain limited by the size and rigidity of the electrode and the restricted distribution of irrigant. In addition, these fluid-enhanced electrodes may not encompass irregular shapes reproducibly, where anatomical features or non-homogeneity in tissue may produce non-uniform treatments (e.g., the presence of vasculature producing the "heat-sink" effect). An additional risk of prior-art externally perfused electrodes is the high probability of irrigant reflux along the path of the applicator, causing undesirable tissue damage. In an embodiment, a helical wire rope structure device is at least "semi-permeable" in one or more noncoated areas, and even in the coated areas the fluid can flow inside the coating because the helical wire rope structure is not solid. The helical wire rope structure is of higher surface area than what could otherwise be achieved through existing single or multi-tined electrodes. An irrigant is more evenly distributed along the device via its porosity and the cavity formed by its insertion, reducing surface charring across its active length to yield a more reliable ablation therapy over time. In addition, the flexible, conforming nature of the device allows the clinician to place irregular shapes for more customizable and precise ablation zones. The system may include flexible and porous devices for improving irrigation-enhanced ablative therapies.

One embodiment of the system comprises the steps of lesion localization via imaging (e.g., CT, MRI, Ultrasound) and device placement/path planning; percutaneous delivery probe insertion and placement through or adjacent to lesion under image guidance; deployment of helical wire rope structure and initial bolus of cooled conductive fluid; ablation energy application with continuous low-flow fluid site-irrigation to procedural endpoints; and retraction and removal of helical wire rope structure via deployment cannula, and reassessment of ablation volume.

Radiofrequency Ablation

RF ablation is a minimally invasive procedure used to thermally destroy tumors. Ablation devices are inserted into or surrounding a tumor, with electrical current (~500 kHz) conducted between the device and large-surface dispersive devices placed on patient skin, or between devices in multipolar configurations. Electrical power is converted into heat by induced ionic vibrations, referred to as the joule effect. These vibrations cause cell death over an affected volume when subjected to temperatures above 60 C for several minutes. Induced high temperature leads to intracellular protein denaturation, the disruption of membrane lipid bilayers, and the coagulative necrosis of tumor cells. RF ablation at lower power may induce mild hyperthermia, whereby tissue is heated above the body temperature to induce physiological effects while not directly producing substantial cell death. Temperatures of 40 to 45 degrees Celsius may be maintained for times up to 1 hour, in contrast to ablative hyperthermia, which achieves temperatures greater than 55 C for shorter durations of 15 to 20 minutes. Hyperthermia treatments may result in physiological (i.e., perfusion) or cellular (i.e. gene expression) changes which improve therapeutic efficacy through localized sensitization in conjunction with a chemotherapeutic. Power may be cycled on and off over an hour-long period as a method of avoiding the transition from mild hyperthermia to ablative hyperthermia.

In an embodiment, RF current, typically a 500 kHz alternating current, can be applied through pushing one or more partially uninsulated thin (20-30 gauge) needles into the bulk of the wire structure device under image guidance. Strength of the metal-to-metal connection may be verified by an associated electrical control system, where there exists a lower impedance for the helical wire rope structure/ground connection compared to the partially uninsulated needle/ ground connection. Said electrical control systems prevent ablation until impedance between helical wire rope structure and ground, or impedance between helical wire rope structure and adjacent device, is below 1000 ohms or above 25 ohms. Needle-based current transfer may be a repeated procedure, facilitated by the secure anchoring of the wire-structure by tissue ingrowth.

RF ablation's clinical efficacy is mediated by creation of an ablative margin surrounding tumors (at about 20%). Tumors may have irregular volumes that limit the use of RF ablation applicators, which may produce spherical or minimally oblong ablation zones. Controlled delivery of the flexible, high geometric-surface-area (GSA) helical wire rope structure enables the creation of complex ablation geometries, more efficiently overlapping unconventional/ non-spherical tumors. Controlled delivery of multiple helical wire rope structures applied around, without directly puncturing the tumor, further increases ablative volumes while avoiding unintentional scattering of tumor cells (tumor seeding.

As a micron-scale conductor, the wire within the helical wire rope structure device will locally produce an electric field and effective zone of heat conduction and transmission into the surrounding target tissue with target tissue fluids, and also acts as a bulk conductor, which also produces an electric field and effective zone of heat conduction. The bulk conduction (electrical/thermal) and radiation of the helical wire rope structure device therefore is the combination of both macro and micro-scale properties.

In various embodiments the system comprises at least one helical wire rope structure, a device delivery cannula, and device interfacing tool, in some embodiments attached to device delivery cannula, in some embodiments connected to one or more internal temperature sensors, an irrigant, in some embodiments a hypertonic saline solution, or another conductive fluid, an irrigant delivery cannula (in some embodiments the same delivery cannula used for helical wire rope structure device placement), a power generator, a system controller, in some embodiments linked to external passive temperature sensors, a programmable microinfusing pump, and a high surface area common device/return patch.

A system for acute (hyperthermic) ablation, in one embodiment, comprises a helical wire rope structure attached to an interfacing element in series with a high frequency (HF) power supply, controller, and one or more sensors, and are coupled to a channel or channels through which a conductive fluid may be introduced into the ablation site.

Another example method of acute (hyperthermic) ablation utilizing a helical wire rope structure uses percutaneous delivery/deployment, (e.g., as framed in FIG. 32), and then application of current to the treatment site with the device, receiving a temperature measurement at the site of the active device, and adjusting the flow rate of the irrigant based on the temperature measurement. Temperature measurement can be obtained by a thermocouple embedded in the tip of the ablation probe or on a separate needle-type device. For example, a sufficiently high temperature can increase risk of tissue desiccation, and the fluid rate may be adjusted to decrease temperature at the surface of the device to avoid excessive carbonization across the entire surface of the helical wire rope structure.

The particular characteristics of the helical wire rope structure may vary in the number and diameter of conductive metal wire strands, strand sizes, and wire packing density. The size of the inner and outer diameters of the helix may vary as well. The interfacing element is electrically conductive and may be physically coupled to the helical wire rope structure (e.g. attached to the injection plunger which is attached in series to a HF power generator/controller, or attached to an external interfacing device e.g. a needle attached in series to a HF power generator/controller). The system may incorporate one or more sensors along/within the helical wire rope structure or the interfacing element for measurement of current, impedance, and temperature. Conductive fluids may include hypertonic (>0.9% w/v) saline, starches, acids, metallic-doped or other ionic hydrogels, or other fluids with greater-than-physiological conductivity. Conductive fluids may be introduced into the ablation site through channels linking to the porous helical wire rope structure, or through external means (e.g. a flexible catheter). Fluids may be pushed using a microinfusing pump, which may be programmable and sensor-feedback-responsive.

Electrolytic (DC) Ablation

Methods which use electrolysis (e.g., by application of direct current) to destroy tissue selectively in the context of tumor ablation are described. Electrolytic ablation (EA) is the process by which cytotoxic species are generated by electrochemical reactions occurring at device surfaces in response to a direct current. In physiological conditions, such reactions create changes in pH, with acidic regions produced near anodes (oxidation) and basic regions produced near cathodes (reduction). A limitation of this technique is the longer time that may be utilized for ablative species to be present in high concentrations, as well as the long times that may be utilized for ablative species to diffuse through tissue.

One embodiment of an EA system comprises a helical wire rope structure device or devices; a device delivery cannula, a device interfacing tool, in some embodiments attached to helical wire rope structure delivery cannula, in some embodiments connected to one or more internal pH sensors; an irrigant, in some embodiments a hypertonic saline solution, or another conductive fluid; an irrigant channel, in some embodiments the same channel used for helical wire rope structure device placement; a DC Supply; a system controller, in some embodiments linked to external passive temperature sensors; a programmable microinfusing pump; and a high surface area common device/return patch.

One embodiment of a method of delivery for acute EA utilizing an injectable, helical wire rope structure device may include formation of one or more cavities through physical means (cannula insertion to target) or use of hydro dissection, followed by delivery (injection) of one or more helical wire rope structures through inserted cannulas into formed cavities, followed by delivery (injection) of a conductive fluid to the sites of ablation through the same or a separate delivery cannula.

Another embodiment of acute EA comprises a helical wire rope structure may include delivery (above) and subsequent application of a voltage between implanted devices or between an implanted device and a surface patch, receiving a pH measurement at the active treatment site, and adjusting the flow rate of the irrigant based on the pH measurement. For example, a low pH measurement at the site of the device, or through a pH measurement taken at the outer edge of the treatment site, may be used as an indicator by a controller to stop an applied voltage/electrolysis.

One example method of chronic comprises a helical wire rope structure include interfacing (e.g., via partially uninsulated needle), delivering an irrigant to the interstitial space, and subsequent application of a voltage between implanted devices or between an implanted device and a surface patch, receiving a pH measurement at the active treatment site, and adjusting the flow rate of the irrigant based on the pH measurement near the site of interest.

Being an indwelling device with a predictable field output allows repeated interfacing and sensitization of tissue through RE to a combination with chemical therapeutics, prior to a hyperthermic or non-thermal ablative treatment. Sensitization using electroporation through the helical wire rope structure decreases the load of drug, reducing side effects and cost.

Energy may be applied to the helical wire rope structure through a specially designed high voltage generator and a secure, well insulated needle interface, as described. Design of power systems for electroporation devices may facilitate the attention to safety due to the high energies accumulated in capacitors and from the delivery of high electrical currents to the patient—both operator and patient are at some risk of electrocution if energy release to the patient is not reliably controlled. The resistive load of a biological tissue varies, and depends on the physical properties of the devices. In the case of the helical wire rope structure, this may be difficult to assess without a preliminary test. Existing electroporation devices which measure a load of more than 50 A will interrupt the pulse sequence, under the assumption that a short circuit or sparking is occurring between devices.

Electrolytic ablation with direct current does not ablate tissue like RF which is generally associated with heat generated that kills tissue. Direct current kills not with heat but by changing the pH in the vicinity of the device to cause cells to leak their contents as the change in acidity leading to the change in pH damages the cell walls and the metabolism of the cells whose walls it does not damage right away. This method has been applied towards the treatment of lung, liver, and pancreatic tumors. It has also been applied in the field of controlled nerve ablation, with nerves lesioned by DC experiencing a rapidly reduced conduction (nerve block). Applied low-voltage DC (<50V) between two or more devices results in electrolysis, generating hydrogen (hydronium, $H_3O^+$) ions at the anode and hydroxide ions at the cathode.

$$Anode: 2H_2O\langle-\rangle O_2 + 4H^+ + 4e^-$$

$$Cathode: 2\ H_2O + 2e^- \langle-\rangle H_2 + 2OH^-$$

Electrolysis also induces the movement of sodium cations towards the cathode and chloride anions towards the anode. This results in the production of sodium hydroxide and hydrogen near the cathode, and hydrochloric acid, oxygen, and chlorine near the anode. The regions surrounding the anode become acidic (pH<6), while the region surrounding the cathode becomes alkaline (pH>9), resulting in non-thermal cell death (pH<4.8, pH>10.6). Additional contributors to cell death in vivo include the generation of reactive oxygen species, though their effect is secondary to that of pH-driven cell death.

Electrolytic ablations offer a great deal of increased precision, shaping well defined ablation margins due to the introduction of toxic levels of acid and base. Selective alteration of the local microenvironment makes it well suited as a modality for the treatment of complex tissue shapes. Helical wire rope structures are able to be placed precisely in user-tailored conformations, making it well suited to treat complex tumor shapes. Ease of multiple placements, such as in the potential case of a multiple helical wire rope structures placed as cathode returns, surrounding a single anode of tailored shape, maximizes the potential of electrolytic lesioning as a potential treatment.

The use of wire structures (helical and non-helical) as an embedded, indwelling implant increases the clinical relevance of EA by permitting the re-lesioning of complex margins without multiple repeated probe insertions.

Measuring in-situ tissue electrical resistance and buffering capacity will further enhance precise lesioning. Physiologic buffering in-vivo will limit the spread of acidic and basic species following treatment completion. Electrolytic ablation may be further mediated by the flow of blood through a tissue, delivering additional buffering species and removing generated acid/base ions.
Electroporation Electroporation, or electro-permeability, is the application of short pulses of strong electric fields to cells and tissues. External electric fields increase transmembrane potential, inducing the formation of nanopores, called poration. Applied voltages of up to 1 kV across devices introduces reversible electroporation (RE), the formation of temporary pores in the cell membrane. RE treatment has applications in gene and drug delivery, where the permeability of the cell membrane allows the entry of molecules that would not otherwise penetrate it. Irreversible electroporation (IRE), applying voltages of up to 3 kV, results in permanent disruption of the lipid bilayer and loss of cell homeostasis. The use of small devices and short, repetitive electric field pulses results in a nonthermal apoptotic, as opposed to necrotic cell death, with a well-demarcated region of ablation and sharp boundaries between treated and untreated zones. IRE spares structures such as bile ducts, nerves, blood vessels. Pore formation does not occur significantly in tissue with higher collagenous content or elastic fiber contents. It affects the membrane of living cells, and does not cause the denaturation or coagulation of proteins typical of thermal ablation. IRE is insensitive to the heat-sink effect. IRE generators may deliver up to 3 kV of energy in up to 100 pulses (an electric field gradient in a 40 cm³ volume of at least 800 V/cm is considered the threshold for irreversible electroporation), with two or more monopolar probes or a single bipolar probe used at a time to create ellipsoid ablation zones. Multi-bipolar configurations increase the size of predictable margins. Currently, many IRE procedures are rapid—however, they may utilize general anesthesia and paralytics, and may implement synchronization of voltage pulsing with the refractory period of the cardiac cycle to avoid arrhythmias.

Creation of membrane nanopores allow permeability of agents such as chemotherapy drugs or macromolecules which would not otherwise cross the cell membrane, thus allowing for an effect upon the cell where there would otherwise be none. This allows for augmented drug/genetic delivery systems. Additionally, if enough power is transferred in a controlled field, IRE occurs (hence irreversible electroporation) with subsequent cell death. This is analogous to ablation, but without the thermal effects which may damage the tissue structure and scaffolding (significant vessels, ducts, and/or other structures). Lowering chemotherapy load for therapeutic benefit (irreversible/reversible electroporation mediated increased cellular permeability) DC or rapid AC concept); low level/chronic stimulation (external stimulator); DC or rapid short burst AC stimulation to induce damage to cancer cell membranes, allowing chemotherapy drugs to be better absorbed at potentially lower concentrations; Chemical cancer therapies may utilize cancerous cells to uptake enough drugs to ensure their destruction. Some chemotherapeutic drugs that would otherwise be effective as a treatment may not have activity due to reduced tumor cellular uptake. Thus, drug doses that are implemented for tumoricidal effect may cause global damage to the surrounding healthy tissue and thus leads to unacceptable toxicity in the subject. Using specific energy delivery methods such as passing DC energy through helical wire rope structures causes damage to the cellular membrane of affected local cells, effectively making the cells more permeable. This technique, with well-placed devices, make tumor cells more susceptible to lower concentrations of cancer treatment drugs, improving effectiveness, reducing negative side effects and reducing cost.

RE, IRE and EA are emerging non-thermal focal therapies. Both electroporation and electrolytic lesioning operate on the principle of an applied DC voltage. Electrolytic treatments are an area of active research in the fields of both tumor ablation and nerve blocks, with studies using bipolar-configured linear devices to cause chemical species evolution near the device surface, causing a pH-mediated localized necrosis. Prior to causing a larger volume localized necrosis, pH-mediated large volume changes (i.e. 2 to 10 mm radially away from the wire structure device) will first cause a neural blocking effect on afferent nerves transmitting and/or processing pain and other sensations from or through the pH-mediated localized volume as well as on efferent nerves transmitting and/or processing action/motor information to, from or through the pH-mediated localized target volume. This temporary reduction of neural activity, akin to a temporary block of neural activity, may be used as a diagnostic tool as well as a tool to determine the charge delivered as direct current injected over treatment time to facilitate the treating of the target and adjacent untargeted tissues. If so desired, the direct current injection may be partially or fully reversed in either charge amount injected or in time current has been applied prior to allow for a partial temporary and a partial permanent nerve or target tissue effect as the outcome of one treatment event. Irreversible electroporation typically may implement a combination of probes, with energy delivered between two probes at a time. Recorded voltages of up to 1 kV are determined reversible electroporation, inducing temporary nanopores in the cell membrane to more easily introduce genes or drugs. Recorded voltages of 1 kV through 3 kV form permanent pores which induce local apoptotic cell death. Current electroporation applicators are 19 gauge needles with 1-4 cm exposed active tips, placed parallel to one another 1-2 centimeters apart.

Microwave

MW ablation is a thermal technique which creates an electromagnetic field surrounding a monopolar device, inducing homogeneous heating and coagulative necrosis. It heats rapidly, reaching higher temperatures than other hyperthermia methods (RF), and can treat larger ablation areas compared to monopolar RF. It achieves higher temperatures faster compared to RF, and is less sensitive to the heat-sink effect. Helical wire rope structure, indwelling, serves as a fiducial marker for clinicians to easily locate and re-evaluate the target site for potential repeat treatments.

High Intensity Focused Ultrasound

HIFU is used to cauterize tissue using 5 $W/cm^2$ or greater power. HIFU has difficulty as a standalone therapy, due to poor rates of complete ablation, resulting in higher rates of recurrence. A helical wire coil as a chronically indwelling implant allows easy relocation and accurate targeting for repeat treatments. HIFU introduces biological effects upon tissue, commonly referred to as, thermal effects and ablation. Typically, this occurs with energy deposition of 5 W/cm2 and greater. Additional biological effects within the sub thermal envelope may enhance drug/gene delivery mechanisms similar to electroporation as discussed herein. Currently HIFU as an ablation technique is not complete enough to be completely curative in treating malignant tumors. HIFU has a good use case for benign tumors such as fibroid tumors of the uterus, because it can be useful to mechanically shrink down the bulk of the tumor. However, while HIFU can shrink a tumor through partial tissue destruction, studies of effectiveness indicate it is unlikely to achieve complete ablation. The failure mode of ablation as a treatment for malignant tumors can be due to microscopic disease that is difficult to image well. Non-fully ablated malignant tumors almost always regenerate and regrow. In an embodiment, the system resonates external ultrasound off the solid focal point of the wire structure device to create thermal energy and thus strengthen the ablative ability of the ultrasound signal. Fiducial marking and visibility provides for accurate tracking for recurrence and retreatment at the target site.

FIG. 1-A is an image of a known electroporation probe and FIG. 1-B is the companion generator, Nanoknife, by AngioDynamics.

FIG. 2 contains four images of known devices 34. FIG. 2-A is an image of a 3 cm Single Active-Tip (Covidien Cool-Tip). FIG. 2-B is a StarBurst Expandable Electrode (Angiodynamics). FIG. 2-C is a Cluster Tri-Electrode 2.5 cm Active Tip (Covidien Cool-Tip). FIG. 2-D is a LeVeen Expandable Anchor Electrode (Boston Scientific). Although FIGS. 2-B and 2-D show expandable patterns, these are deterministic and do not allow customized shaping during a clinical procedure.

FIG. 3-A is an image of cadaver tissue with the end of a known RF ablation probe 34 inserted to a subcutaneous point in the tissue to be ablated. FIG. 3-B is an image of the same cadaver after ablation and removal of the probe and showing the pattern of ablation 35 is limited to near the end of the probe.

FIG. 4-A is an image of cadaver tissue with a helical wire rope structure device implanted subcutaneously prior to RF ablation. FIG. 4-B shows the end of a gold wire in the wire structure device excised and clamped directly to an RF probe 34. FIG. 4-C is an image of the ablation pattern 35 in the cadaver tissue from the wire structure device.

FIG. 5 is a photo showing a comparison of ablation patterns 35 from the known device in FIG. 3-B and from a wire structure device in FIG. 4-C for the same duration and same amount of RF energy. The known device pattern is shown by axes A (16.7 mm) and B (10.6 mm) with an approximate total area of 139 $mm^2$, and the ablation pattern generated from an embodiment of the system is shown by axes C (33.6 mm) and B (23.0 mm) with an approximate total are of 607 $mm^2$.

Figure 6:
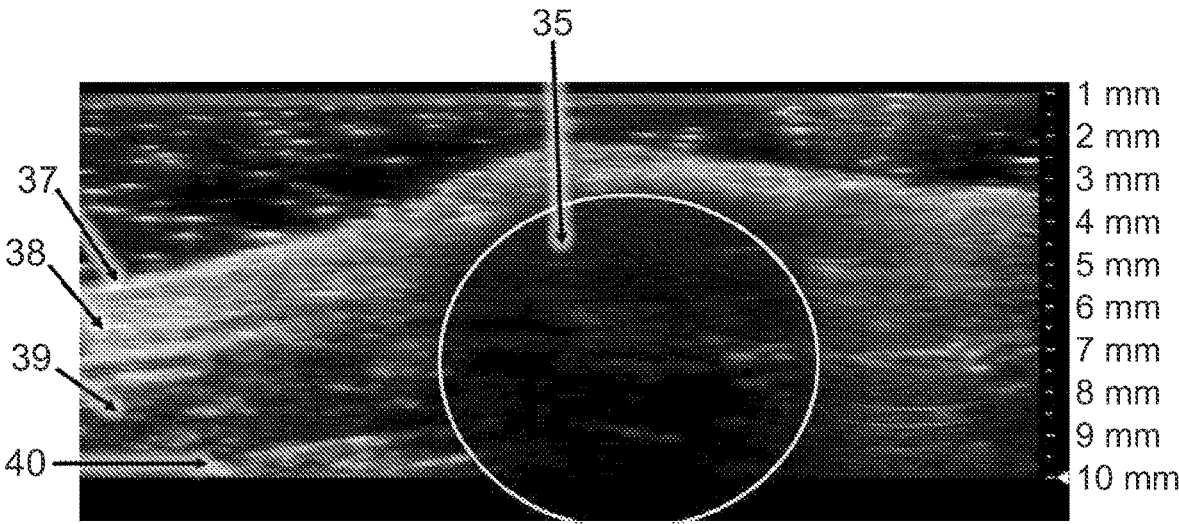
FIG. 6 is an ultrasound visualization of a pattern of RF ablation for 20 watts and 120 seconds.

FIG. 6 is an ultrasound visualization of a pattern of RF ablation 35 for 20 watts and 120 seconds. The tissue layers shown are epidermis 37, dermis 38, adipose/subcutaneous fat 39, and fascia/muscle 40.

FIG. 7-A is transdermal imaging of a subcutaneously implanted helical gold wire rope structure device in a J-hook shape 36, and FIG. 7-B is the same image with cross sections 8-8, 9-9 and 10-10 labeled.

Figure 8:
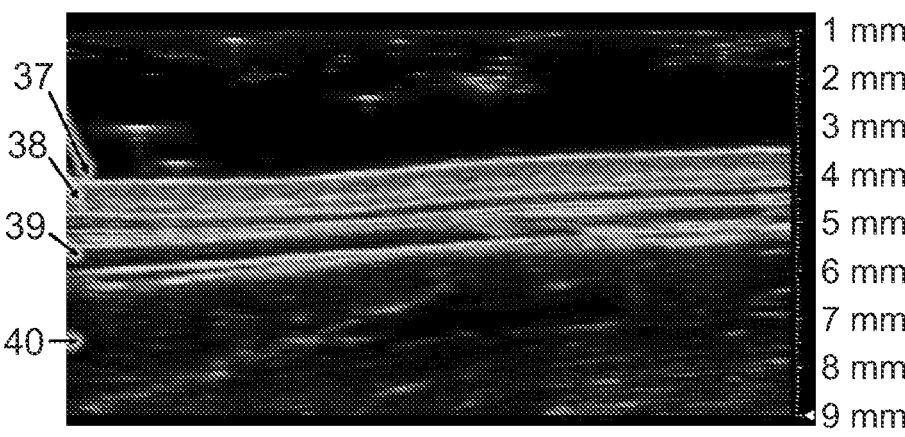
FIG. 8 is an ultrasound image of the cross section 8-8 in FIG. 7-B showing no wire structure device (prior to its placement), taken with a VEVO 3100 system and 45 MHz probe.

FIG. 8 is an ultrasound image of the cross section 8-8 in FIG. 7-B showing none of the wire structure device, taken with a VEVO 3100 system and 45 MHz probe. Layers of tissue are the epidermis 37, dermis 38, adipose/fat tissue 39 and fascia/muscle 40.

Figure 9:
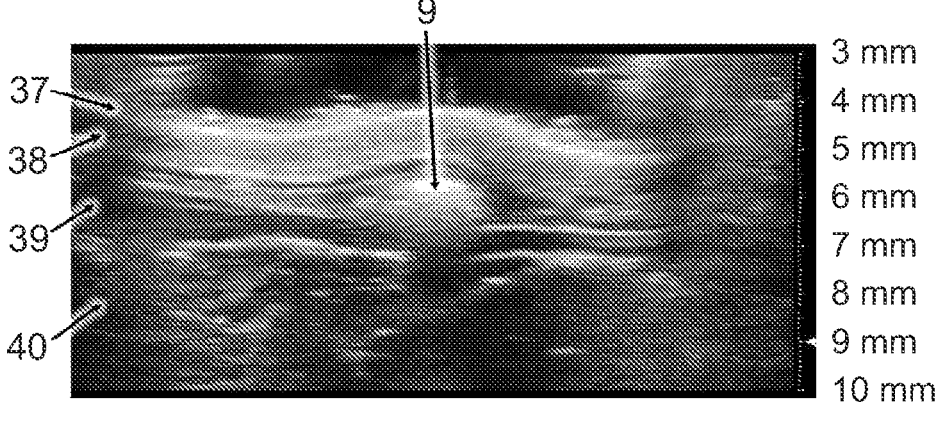
FIG. 9 is an ultrasound image of the cross section 9-9 in FIG. 7-B showing the long shaft of the J, taken with a VEVO 3100 system and 45 MHz probe.

FIG. 9 is an ultrasound image of the cross section 9-9 in FIG. 7-B showing the substantially linear portion 9 of the J 36, taken with a VEVO 3100 system and 45 MHz probe. Layers of tissue are the epidermis 37, dermis 38, adipose/fat tissue 39 and fascia/muscle 40.

Figure 10:
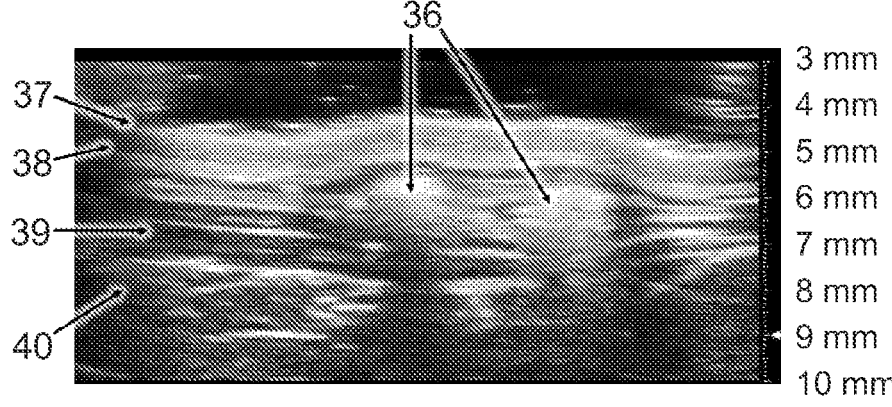
FIG. 10 is an ultrasound image of the cross section 10-10 in FIG. 7-B showing the long shaft and hook of the J, taken with a VEVO 3100 system and 45 MHz probe.

FIG. 10 is an ultrasound image of the cross section 10-10 in FIG. 7-B showing the hook of the J 36, taken with a VEVO 3100 system and 45 MHz probe. Layers of tissue are the epidermis 37, dermis 38, adipose/fat tissue 39 and fascia/muscle 40.

Figure 11:
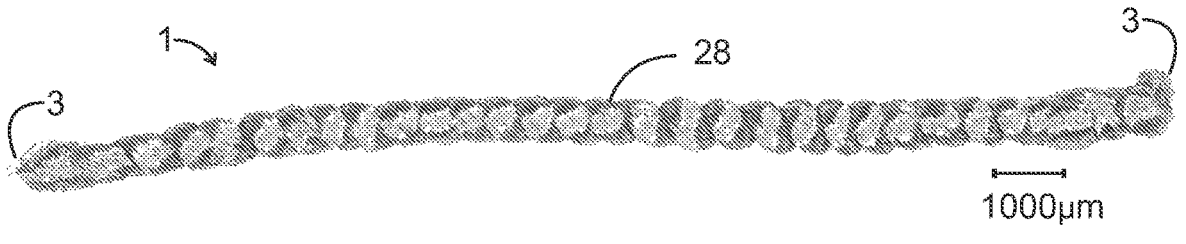
FIG. 11 is an image (15.6×) of one embodiment of the injectable device with the helical wire rope structure after removal of the guidewire.
Figure 12:
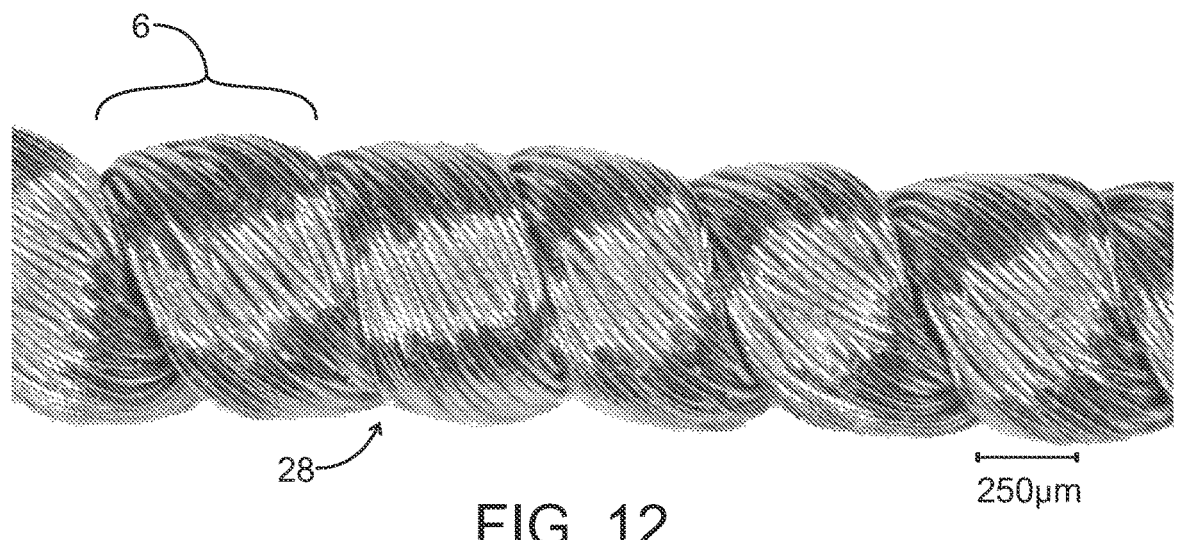
FIG. 12 is a closer image (100×) of a middle portion of the helical wire rope structure of FIG. 11.
Figure 13:
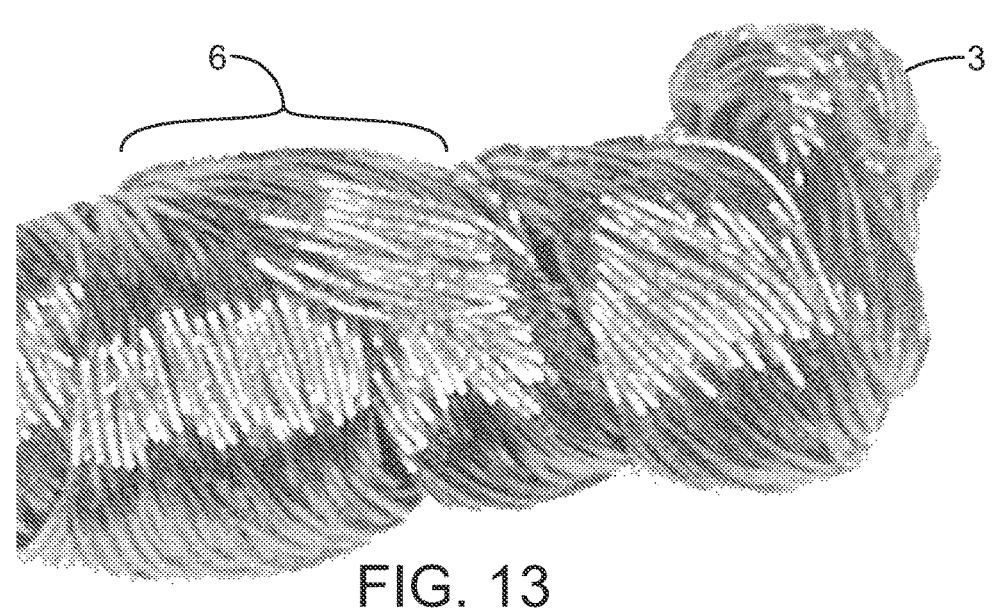
FIG. 13 is a closer image (100×) of a rounded end of the helical wire rope structure of FIG. 11.
Figure 14:
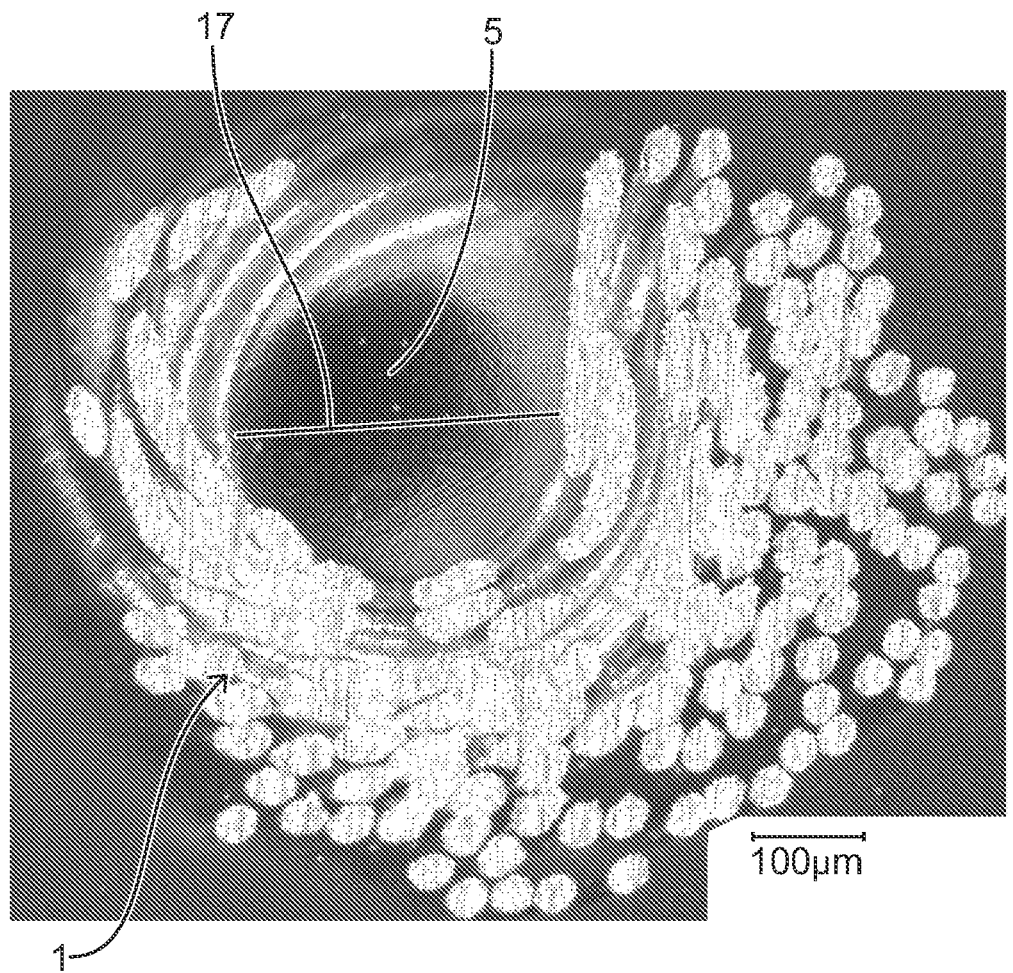
FIG. 14 is an image (300×) of a latitudinal cross-section after being cut of a device comprising a helical wire rope structure comprising a wire rope comprising 100 strands of 25 micron diameter gold wire.
Figure 15:
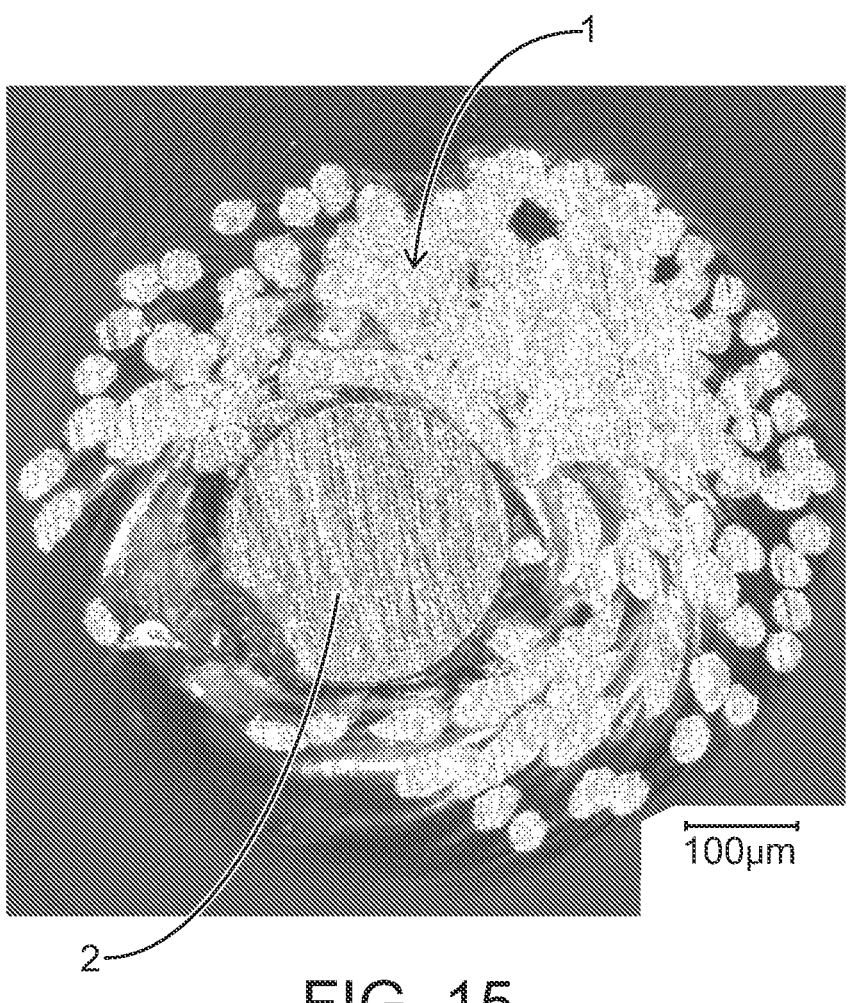
FIG. 15 is the same device as in FIG. 14 before the 0.25 mm guidewire was removed.

FIG. 11 is an image (15.6×) of one embodiment of the injectable device with the helical wire rope structure having ends 3 and a middle portion 28 after removal of the guidewire. The wire rope is 100 strands of 25 diameter micron gold wire, and the helical wire rope structure has an approximate outer diameter of 0.75 mm. Overall length is approximately 2 cm and is made from 6 meters of continuous gold wire. FIG. 12 is a closer image (100×) of a middle portion 28 of coils 6 of the helical wire rope structure 1 of FIG. 11. FIG. 13 is a closer image (100×) of a rounded end 3 and coils 6 of the helical wire rope structure 1 of FIG. 11. FIGS. 12 and 13 show the irregular position of strands among the coils and at the ends. FIG. 14 is an image (300×) of a latitudinal cross-section of a device comprising a helical wire rope structure with an inner diameter 17 and a hollow core 5 comprising a wire rope comprising 100 strands 4 of 25 micron diameter gold wire. Some of the strands, such as the outer ones are looser than would be the case prior to the cut. FIG. 15 is the same device as in FIG. 14 before the 0.25 mm guidewire 2 was removed.

Figure 16:
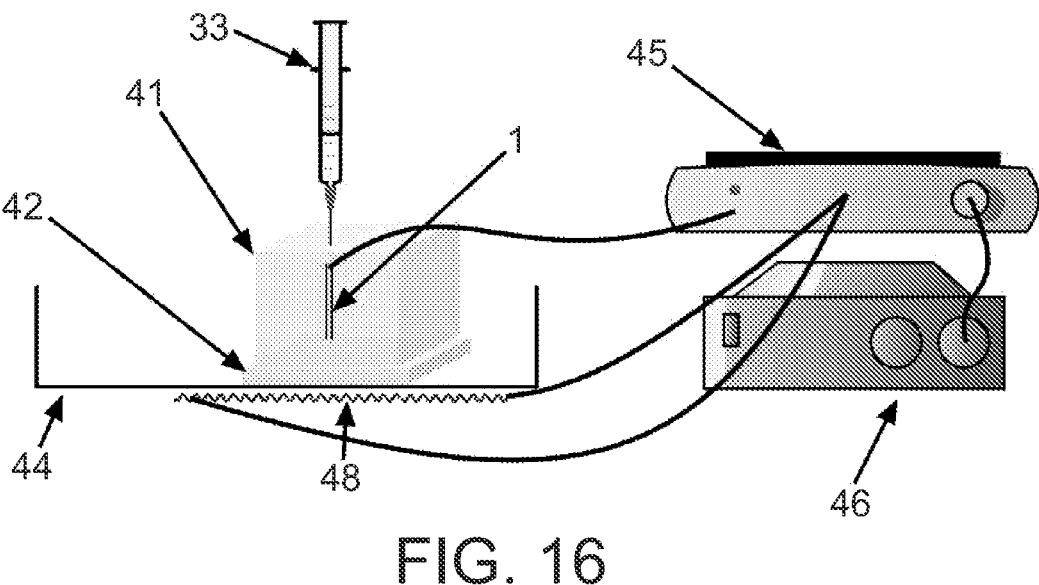
FIG. 16 is an RF ablation experimental set-up.

FIG. 16 is an RF ablation experimental set-up. The helical wire rope structure device is either injected via dispenser or may be pre-embedded into a temperature sensitive gel phantom. Connection between RF generator 46 and helical wire rope structure 1 may be made via direct contact using, for example, a 30-gauge needle. A 15-gauge needle 33 delivers the helical wire rope structure 1 into a gel phantom 41 contacting an electrode gel 42 connected to a grounding plate 44 and grounding pads 48 connected to a switching controller 45 connected to the generator 46.

Figure 17:
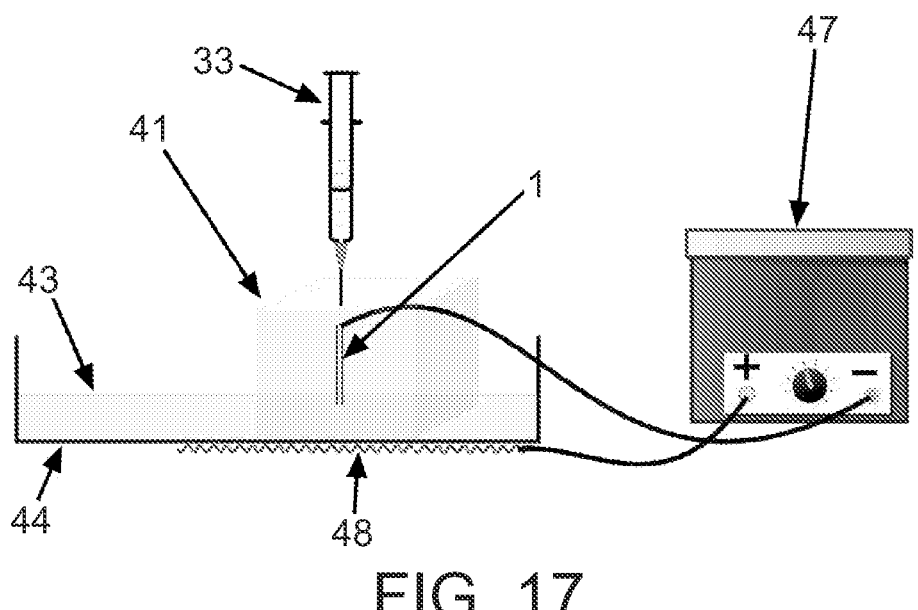
FIG. 17 is a DC ablation experimental set-up.

FIG. 17 is a DC ablation experimental set-up. The helical wire rope structure device 1 is either injected via a dispenser 33 or may be pre-embedded in a pH sensitive gel phantom 41. The negative terminal of the DC supply 47 is attached to a helical wire rope structure device 1 via direct contact (30 g needle). The positive terminal is attached grounding pads 48 connected to the saline-filled grounding plate 44 containing saline 43 for return.

Figure 18:
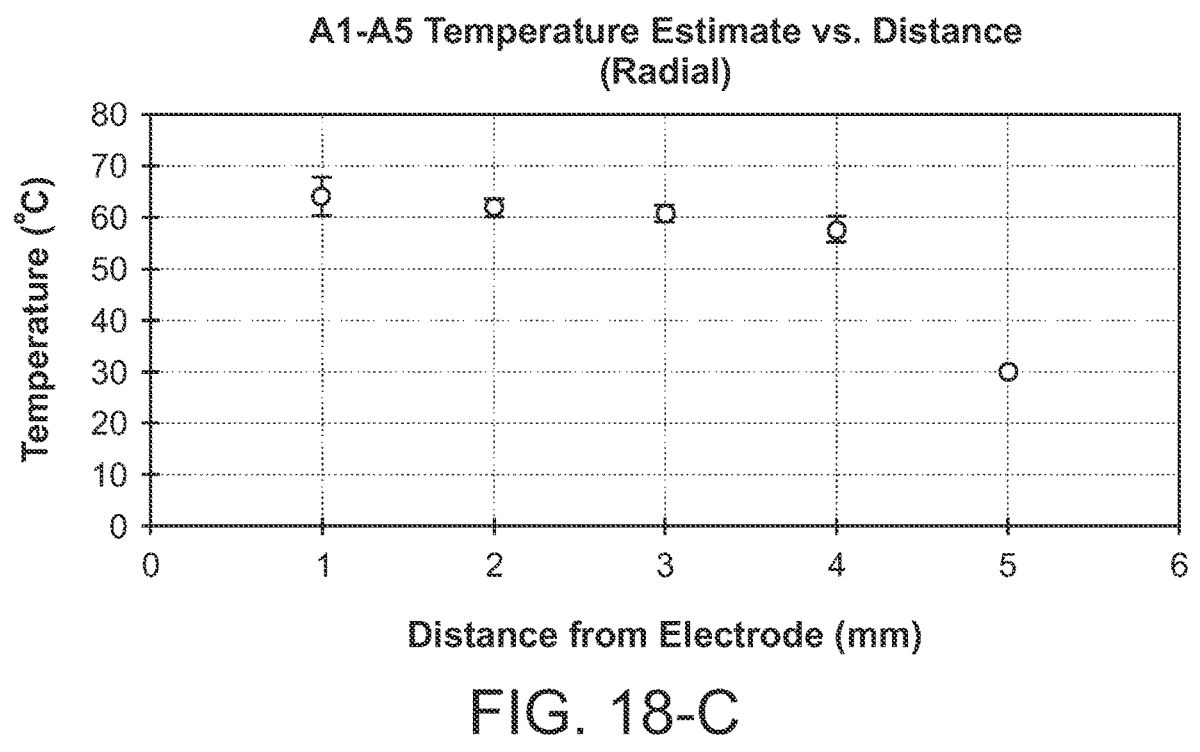

FIG. 18 addresses post-experiment image-based temperature estimation in application of RF energy. FIG. 18-A is an image of an ablative zone 35 effected by a 2 cm-length helical wire rope structure 1 subjected to 40 W power over two minutes. FIG. 18-B shows temperature estimation based on Red/Green/Blue value found 2 mm from device site compared to Red/Green/Blue value of control set across 25-70 degrees Celsius. FIG. 18-C shows temperature estimation vs. distance at sites 1-5 mm from the center of the ablative zone 35.

Figure 19:
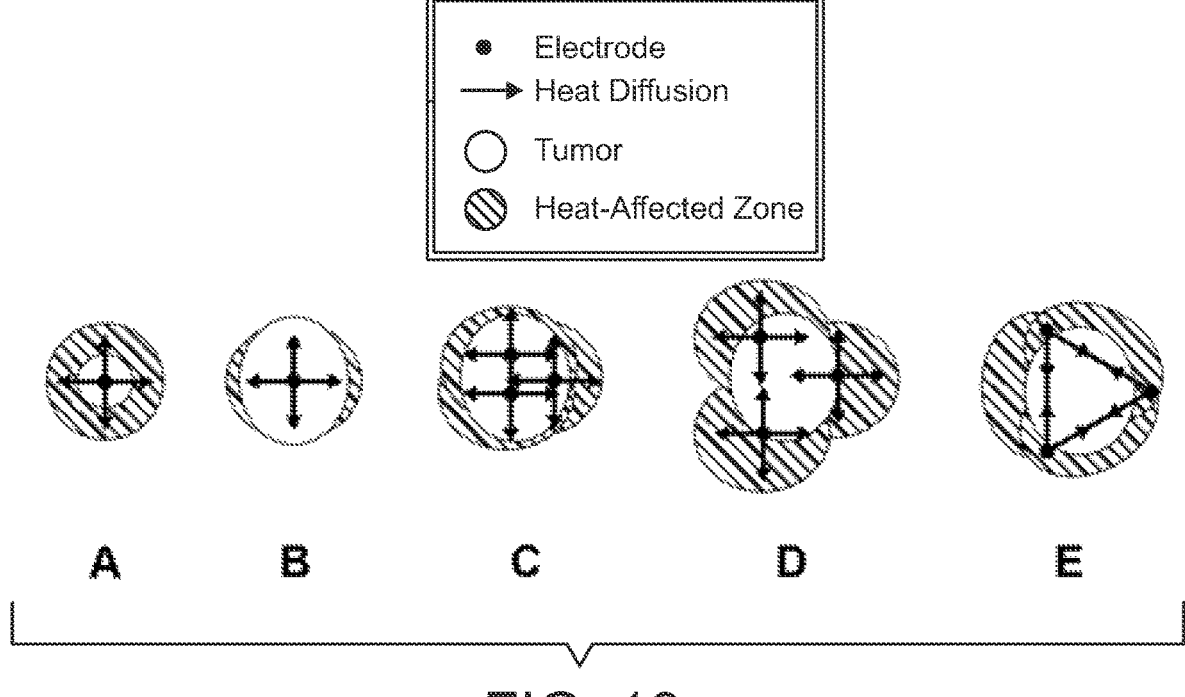
FIG. 19 contains diagrams showing currently known electrode placement and heat dispersion—bird's eye view.

FIG. 19 contains diagrams of existing electrode 34 placement and heat dispersion. FIG. 19-A shows linear electrode placement, radial heat dispersion for a small (<3 cm) tumor 15, and complete ablation. FIG. 19-B shows linear helical wire rope structure placement, radial heat dispersion for a large (>3 cm) tumor 15, but incomplete ablation. FIG. 19-C shows multiple probe placement (intratumorally) configured to cover larger spheroid tumor. FIG. 19-D shows alternative multi-probe arrangement, inconsistent tumor margin for intertumoral placement. FIG. 19-E shows "no touch" ablation, probes arranged outside the tumoral space, with current/heat diffusion running between one or more electrodes to achieve consistent tumor margin. Heat affected zone is shown with cross-hatching.

Figure 20:
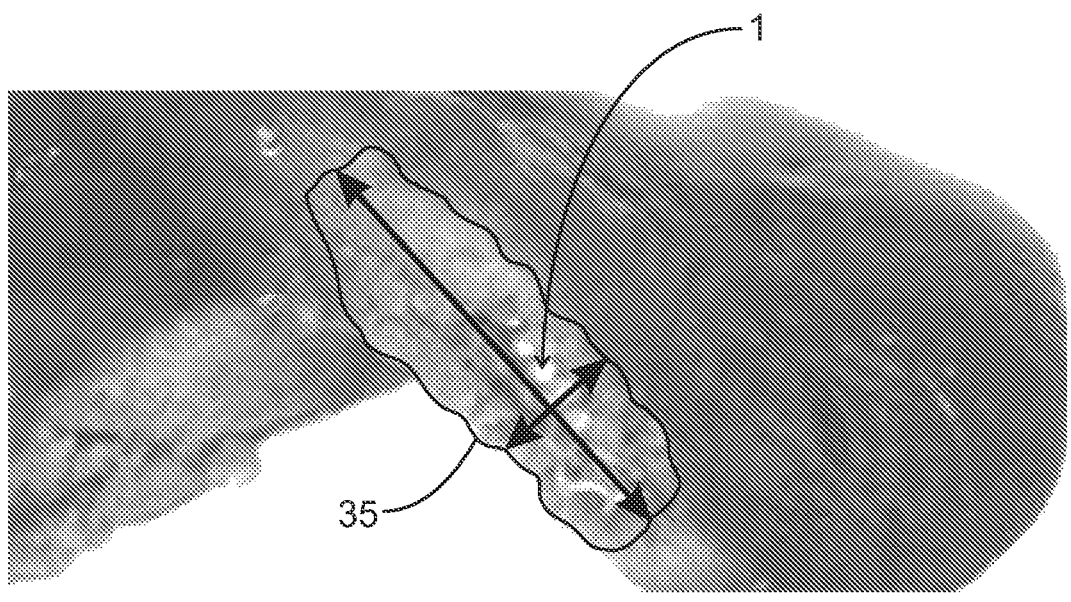
FIG. 20 is an image of rat liver left lobe subject to 1 cm helical wire rope structure device placement and RF ablation at 20 W over 1 minute, and the ablation pattern.

FIG. 20 is an image of rat liver left lobe subject to 1 cm helical wire rope structure 1 placement and RF ablation at 20 W over 1 minute. The arrows show the extent of the ablation pattern 35: width of ~3 mm, and length of ~15 mm.

Figure 21:
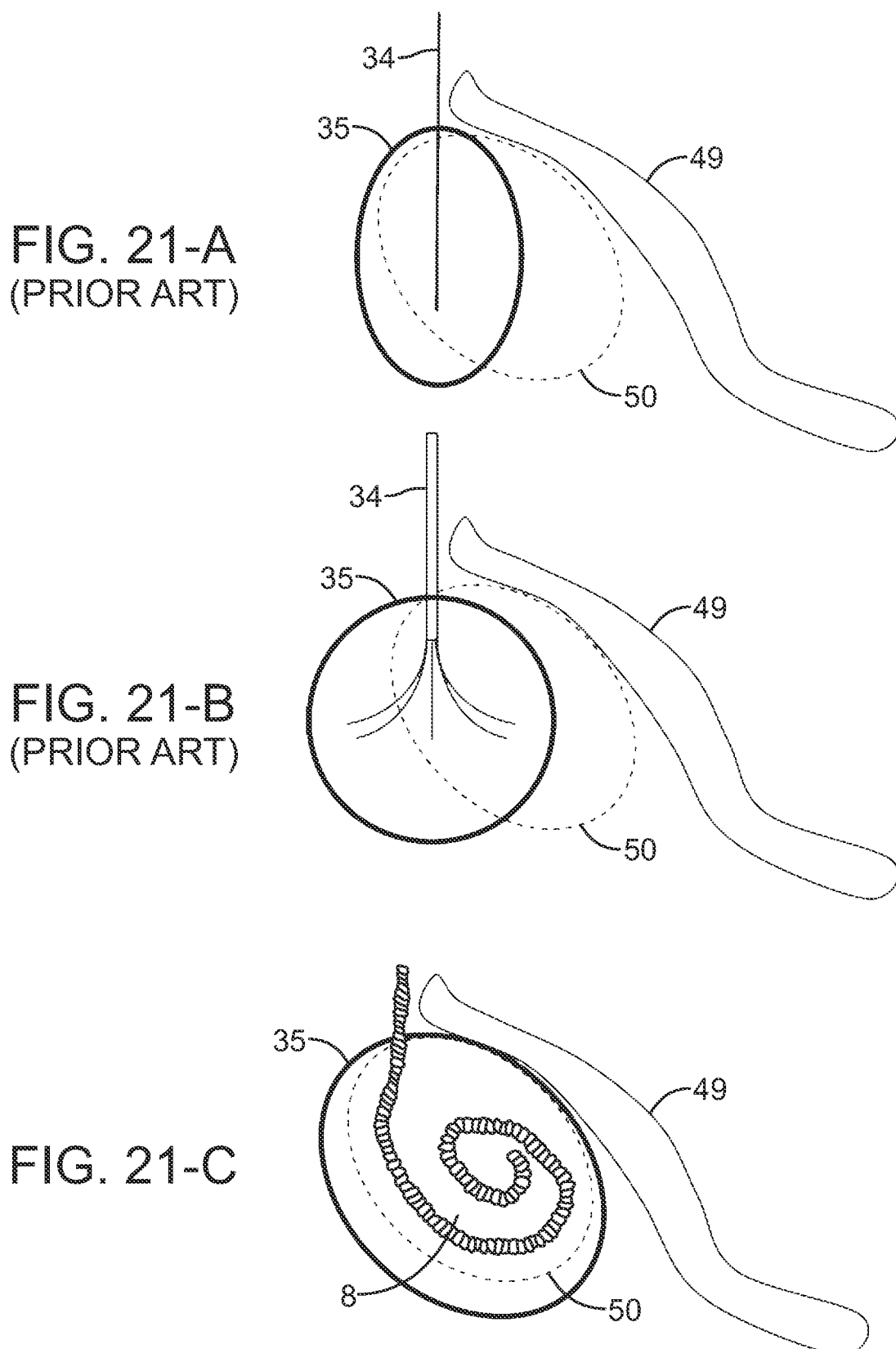
FIGS. 21-A, 21-B and 21-C are three schematics showing the benefit of "around a corner" procedures for a tumor (in dotted lines) shielded by a blood vessel comparing current ablation devices and outcomes, compared to the current devices.

FIG. 21 contains three schematics for "around a corner" procedures for a tumor (in dotted lines) shielded by a blood vessel 49 comparing existing ablation devices and outcomes with an embodiment of the system and outcome. FIG. 21-A is a schematic of a known single probe 34 and its pattern 35 (oval with solid line) which affects a portion of the tumor 50. FIG. 21-B is a schematic of a known single probe 34 with a starburst and its pattern 35 (circle with solid line) which affects a portion of the tumor. FIG. 21-C is a schematic of a helical wire rope structure device 1 and its ablation pattern 35 (tilted larger oval with solid line) which affects the tumor 50. By introducing the helical wire rope structure into a tumor in the shape of the tumor and close to the center line of the tumor (while staying far enough away from one or more structures such as the blood vessel that is not to be damaged by the application of RF ablation for example), a treatment may be provided to a patient that would otherwise not be possible to treat the tumor and leave the blood vessel intact. Similar scenarios are a complex shaped tumor in difficult regions to access with a "straight" ablation probe.

Figure 22:
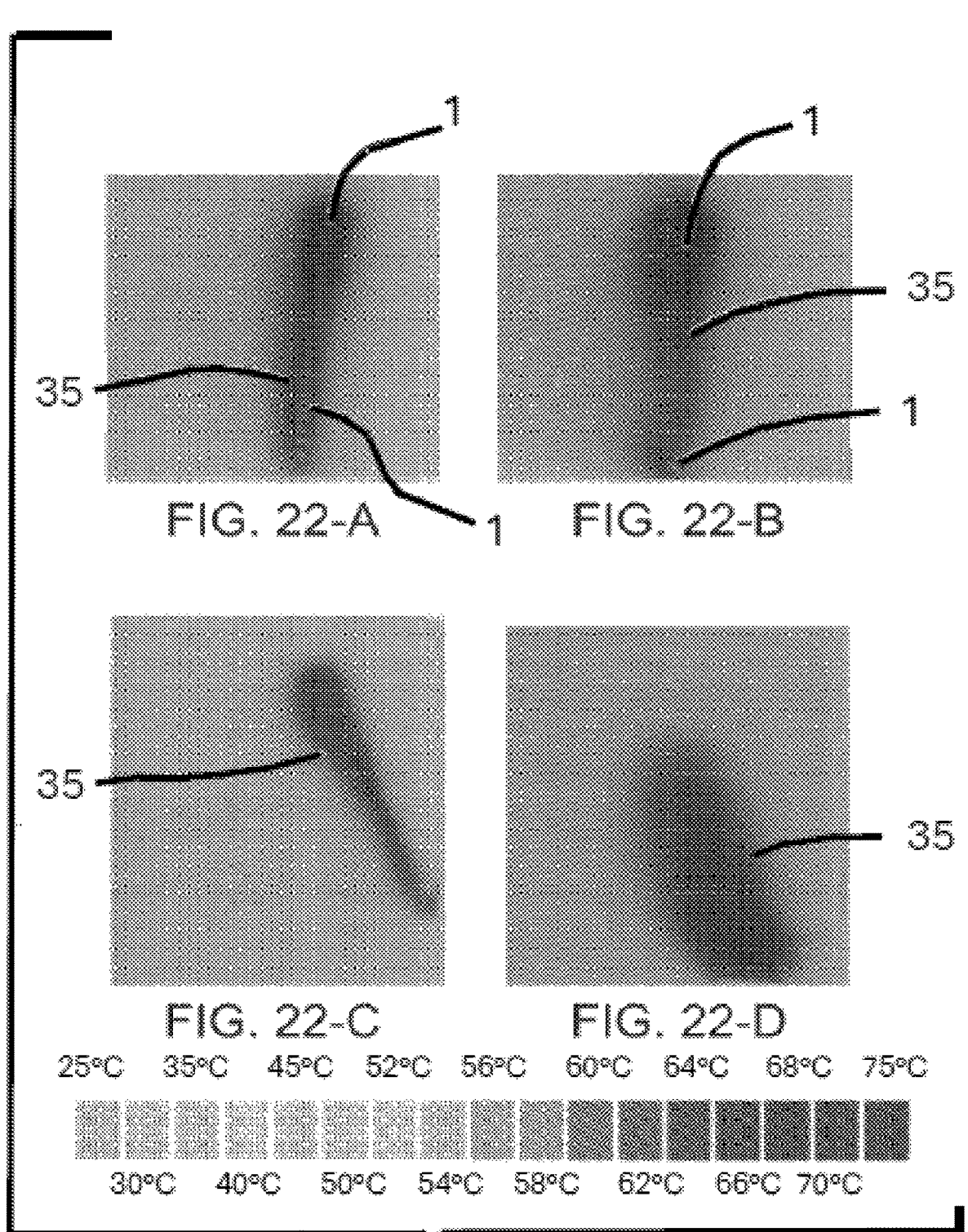
FIG. 22 contains four images of patterns of radiofrequency ablation for linear helical wire rope structures in tissue-mimicking PAG phantoms laced with a thermochromic ink, along with a temperature scale.

FIG. 22 contains four images of radiofrequency ablation zones 35 for linear portion 9 of a helical wire rope structure 1 in tissue-mimicking PAG phantoms laced with a thermochromic ink, along with a temperature scale. FIG. 22-A received 10 watts for 60 seconds, FIG. 22-B received 10 watts for 120 seconds, FIG. 22-C received 20 watts for 60 seconds, and FIG. 22-D received 20 watts for 120 seconds.

Figure 23:
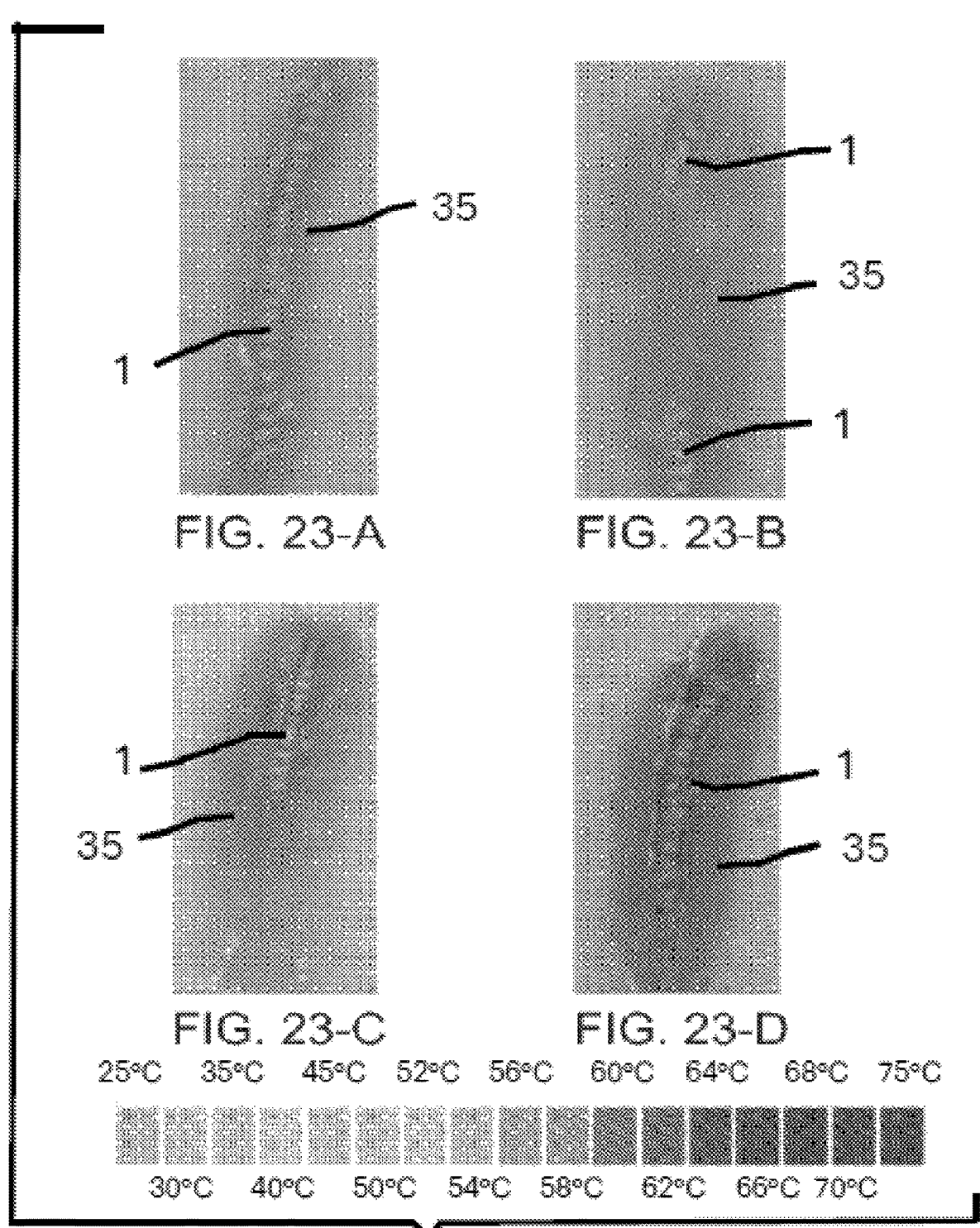
FIG. 23 includes four images of ablation with a substantially linear helical wire rope structure device in cadaver tissue at differing energy and durations.

FIG. 23 includes four images of ablation with a substantially linear portion 9 of a helical wire rope structure 1 in cadaver tissue as follows: FIG. 23-A, 20 watts for 60 seconds; FIG. 23-B, 20 watts for 120 seconds; FIG. 23-C, 40 watts for 60 seconds; and FIG. 23-D, 40 watts for 120 seconds.

Figure 24:
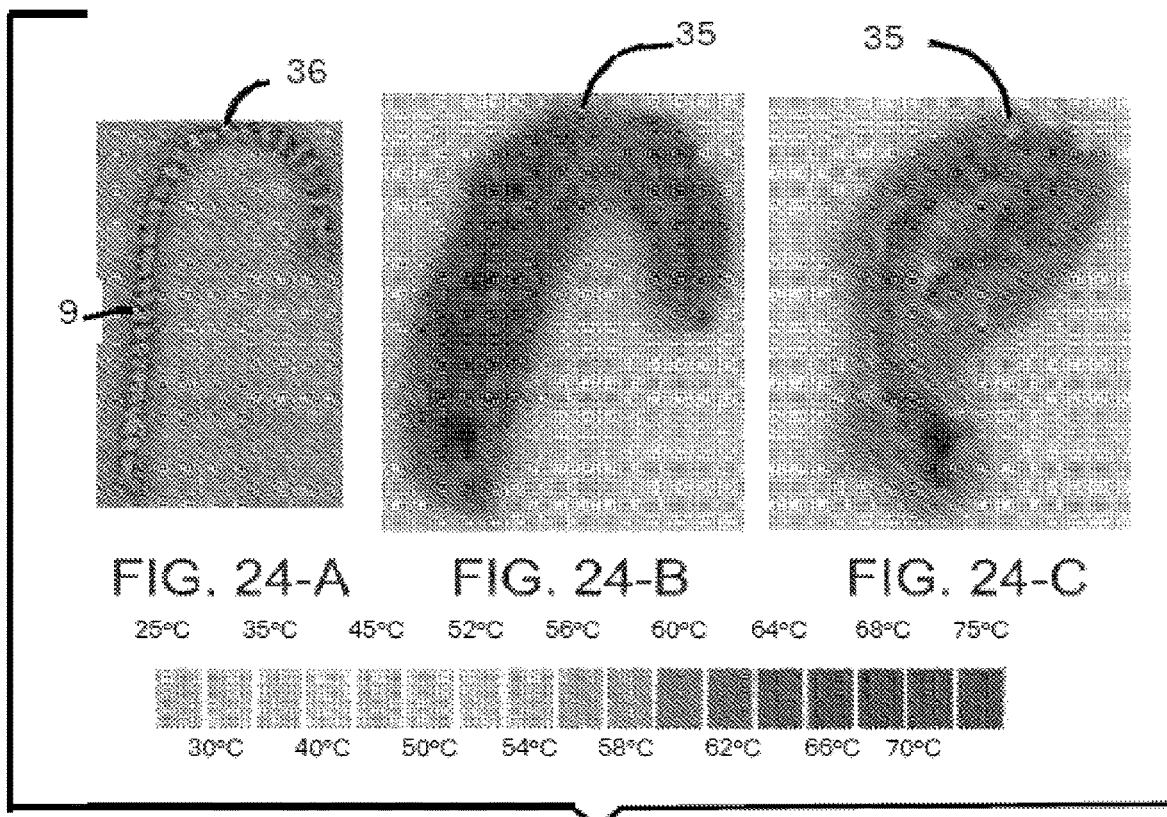
FIG. 24 contain three images of a hooked helical wire rope structure, the center and left images having ablation patterns with RF energy in tissue-mimicking PAG phantoms during different durations at similar scale.

FIG. 24 contains images of curved ablation patterns 35 with RF energy in tissue-mimicking PAG phantoms. FIG. 24-A is a photo of a helical wire rope structure in "hook" 36 conformation prior to implantation. FIG. 24-B shows the implanted helical wire rope structure of FIG. 24-A and the affected pattern 35 after being subjected to 40 watts of over 60 seconds. FIG. 24-C shows the same implanted helical wire rope structure 1 subjected to 40 watts over 120 seconds, showing a larger affected pattern 35 than in FIG. 24-B. The focal ablative region expands from the center of curvature of the implanted helical wire rope structure.

Figure 25:
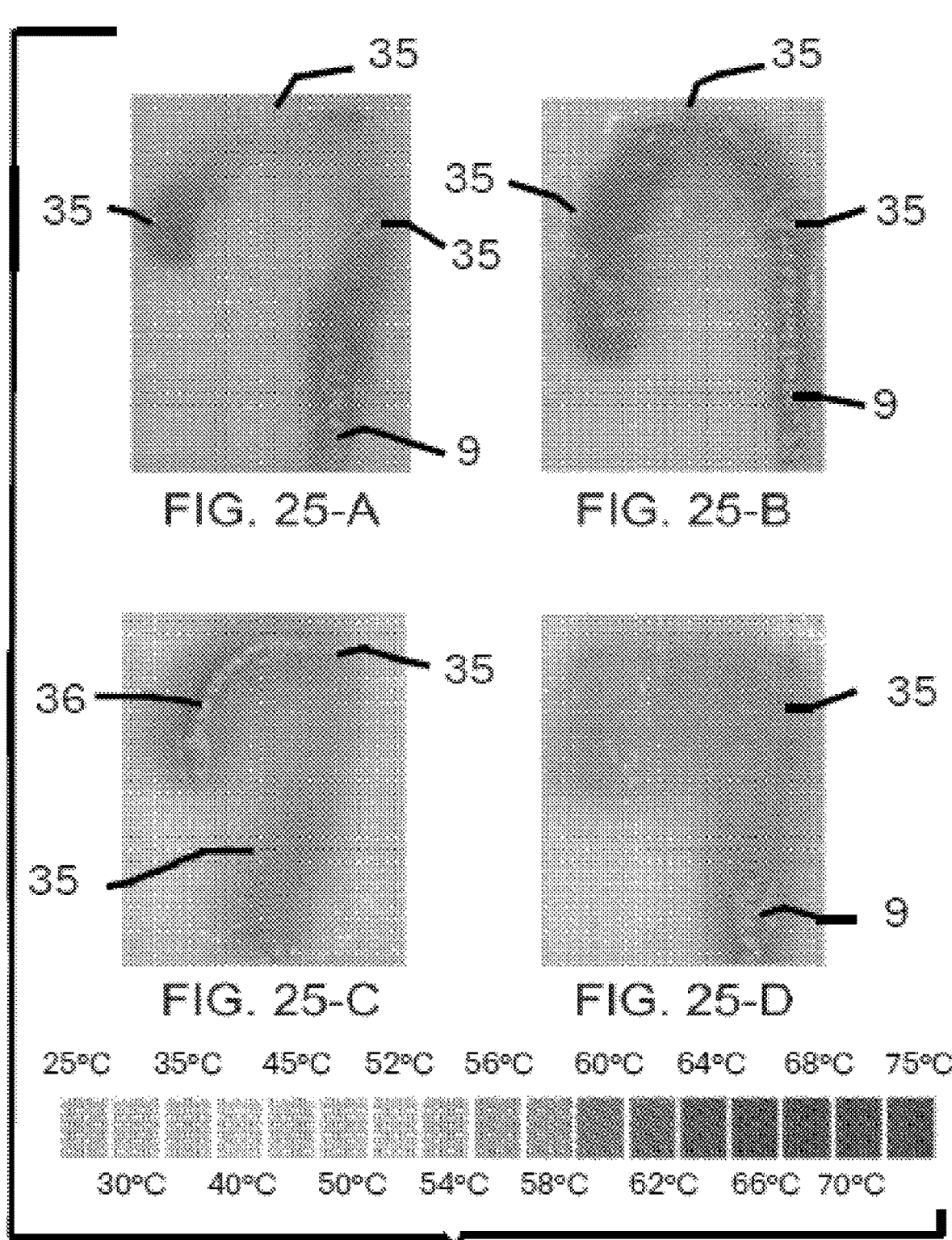
FIG. 25 includes four images of ablation with a J-hook shaped helical wire rope structure device in cadaver tissue at differing energy and durations.

FIG. 25 includes four images of ablation patterns 35 resulting from a J-hook 36 shaped helical wire rope structure device in cadaver tissue as follows: FIG. 25-A, 20 watts for 60 seconds; FIG. 25-B, 20 watts for 120 seconds; FIG. 25-C, 40 watts for 60 seconds; and FIG. 25-D, 40 watts for 120 seconds.

FIG. 26-A, FIG. 26-B, FIG. 26-C and FIG. 26-D are images of two linear helical wire rope structures 9 coupled to the negative terminal of a DC power supply for 0, 60, 300 and 600 seconds, respectively, embedded into a tissue mimicking PAG phantom laced with a pH indicator. The gel phantom is in a container surrounded by saline 43, to which the positive terminal of the power supply is connected such that the saline acts as the return. 10V DC is supplied over the course of 600 seconds and a pH decrease due to the production of acidic species (H+, HCl in particular) is observed across both helical wire rope structures emanating radially, alongside oxygen gas evolution (bubbles). Through use of a battery or a DC power supply set to a constant potential, the negative terminal may be connected via needle or partially insulated clip to anode (helical wire rope structure 1). The cathode (positive terminal) may be connected to an adjacent site, either a conductive bath or a tangentially placed device.

Figure 27:
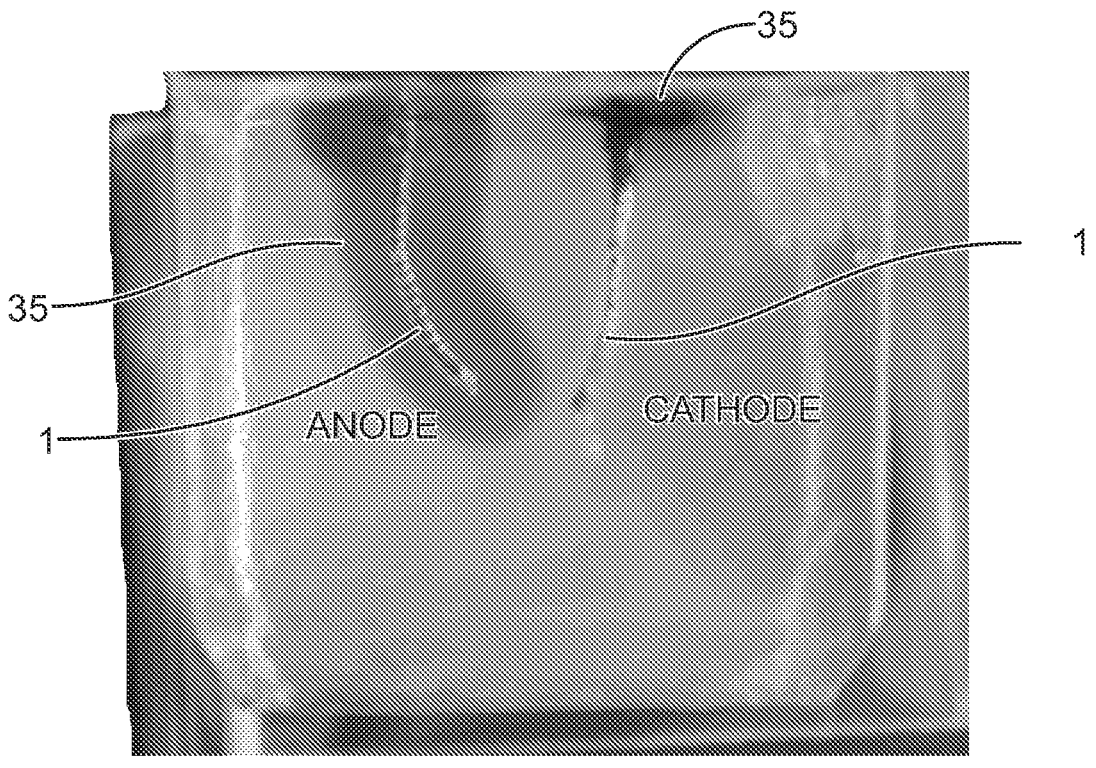
FIG. 27 is an image of electrolysis-induced local pH change and oxygen gas evolution surrounding multiple helical wire rope structure anodes embedded in pH sensitive tissue-mimicking phantom, the result of applied DC voltage between anodes and saline bath return.

FIG. 27 is an image of electrolysis-induced local pH change and oxygen gas evolution surrounding multiple helical wire rope structure anodes embedded in pH sensitive tissue-mimicking phantom, the result of applied DC voltage between anodes and saline bath return. Helical wire rope structure, electrolysis-induced local pH decreases at anode (left) and pH increases at cathode (right), accompanied by surrounding oxygen and hydrogen gas evolution at anode and cathode, respectively, are the result of applied DC between anode and cathode return. The structure of the anode emphasizes that the helical wire rope structure is capable of non-linear pH change geometries.

Figure 28:
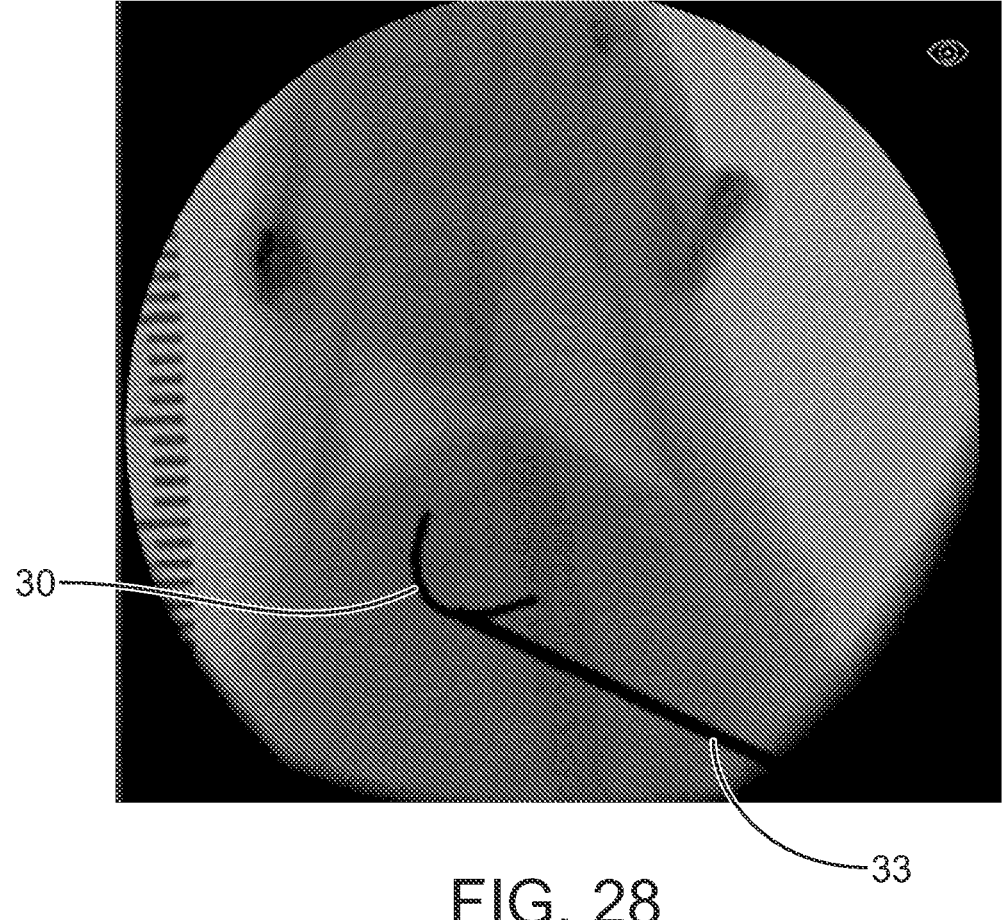
FIG. 28 is a fluoroscopy image of a curved helical wire rope structure embedded near rodent liver, with a partially insulated stainless steel interfacing needle approaching.

FIG. 28 is a fluoroscopy image of a curved 30 helical wire rope structure embedded near rodent liver, with a partially insulated stainless steel interfacing needle approaching.

Figure 29:
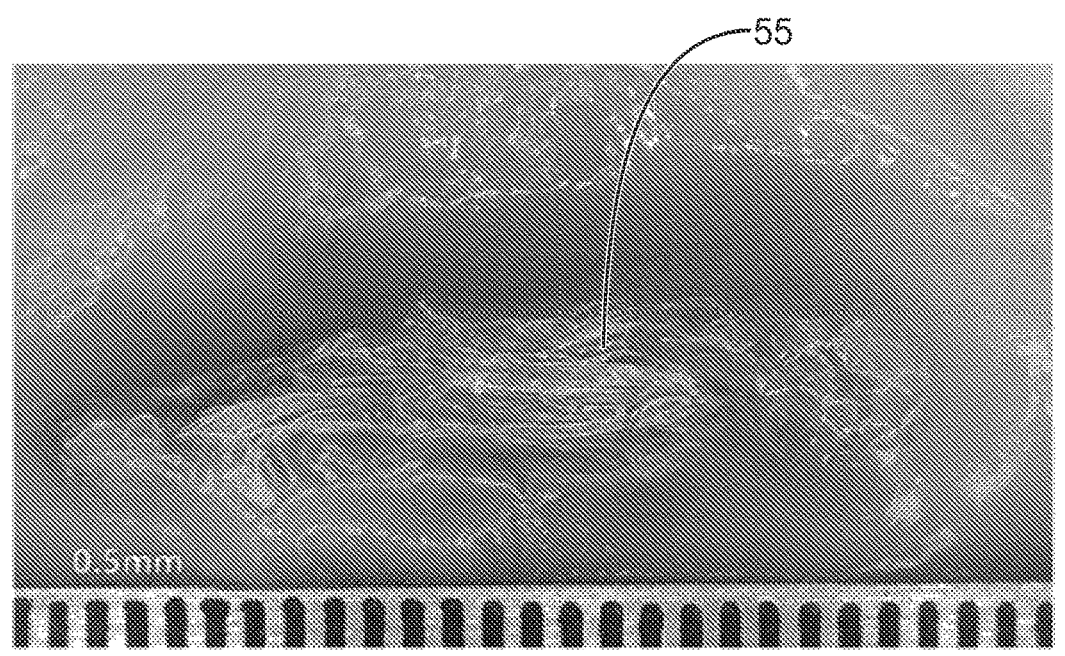
FIG. 29 and FIG. 30 are images of non-helical wire structures implanted in tissue. (These are identical to FIGS. 40 and 41 from PCT '374).
Figure 30:
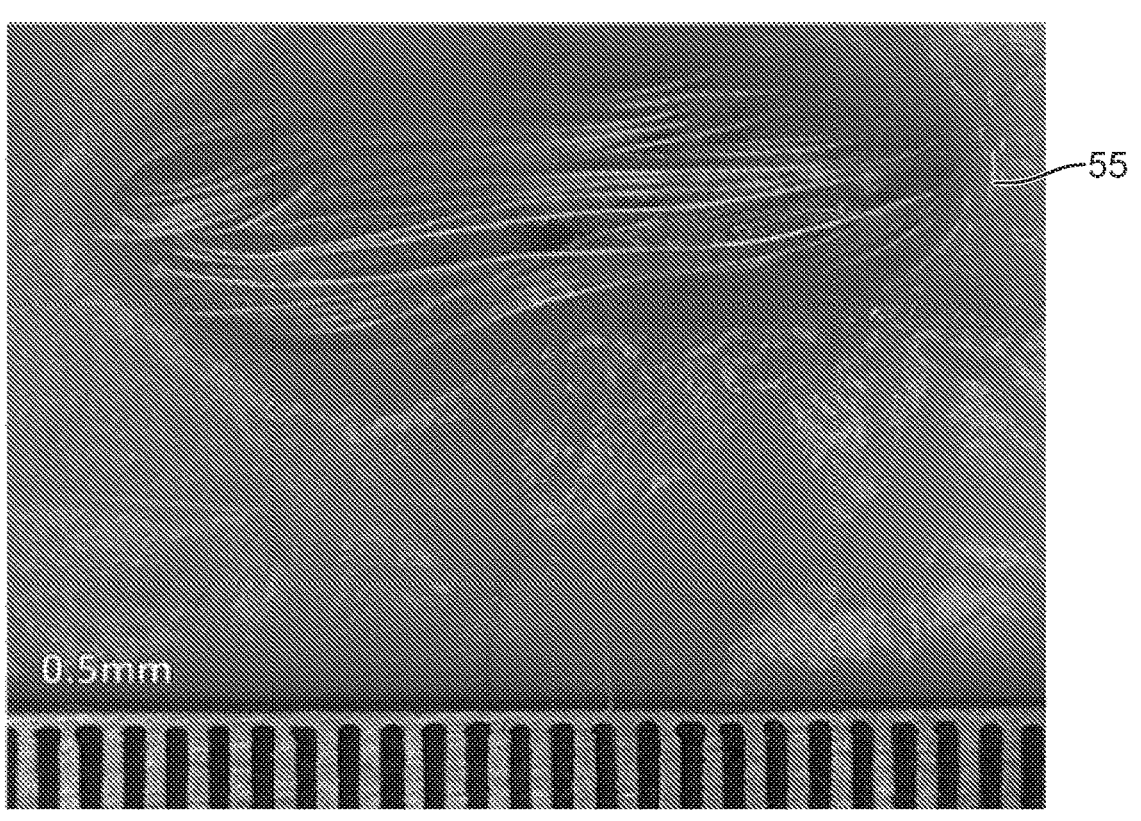
Figure 40:
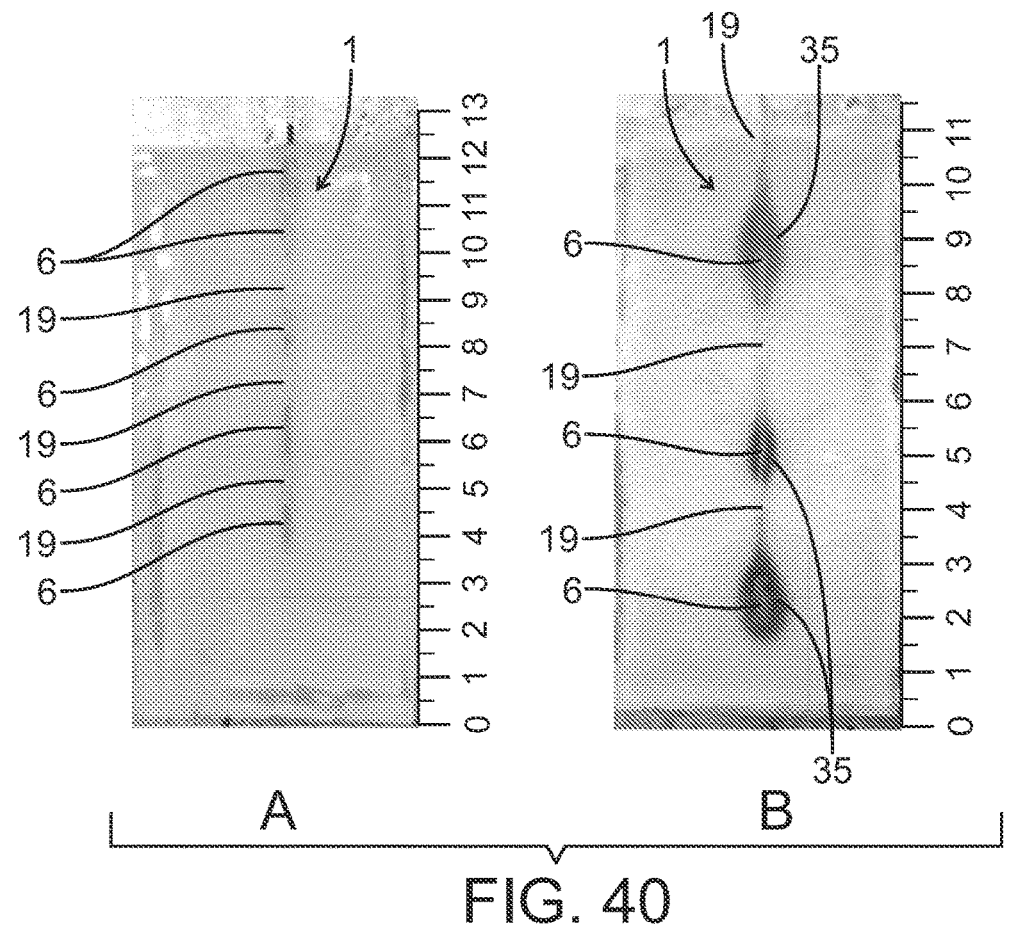
FIG. 40-A and FIG. 40-B are images showing how intermittent coating areas produce an intermittent ablation pattern in heat responsive gel in FIG. 40-B. whereby an insulative heat-shrink polymer coats the helical wire rope structure intermittently and creates ablation patterns 35 (thermal or electrochemical) at coils in the noncoated areas while maintaining tissue integrity near coated sections, which are high impedance and not exposed to ionic environments.

FIG. 29 and FIG. 30 are images of non-helical wire structures implanted in tissue. (These are identical to FIGS. 40 and 41 from PCT '374). Elsewhere herein the relative advantages of non-helical wire structures are discussed.

Figures 31A, 31B:
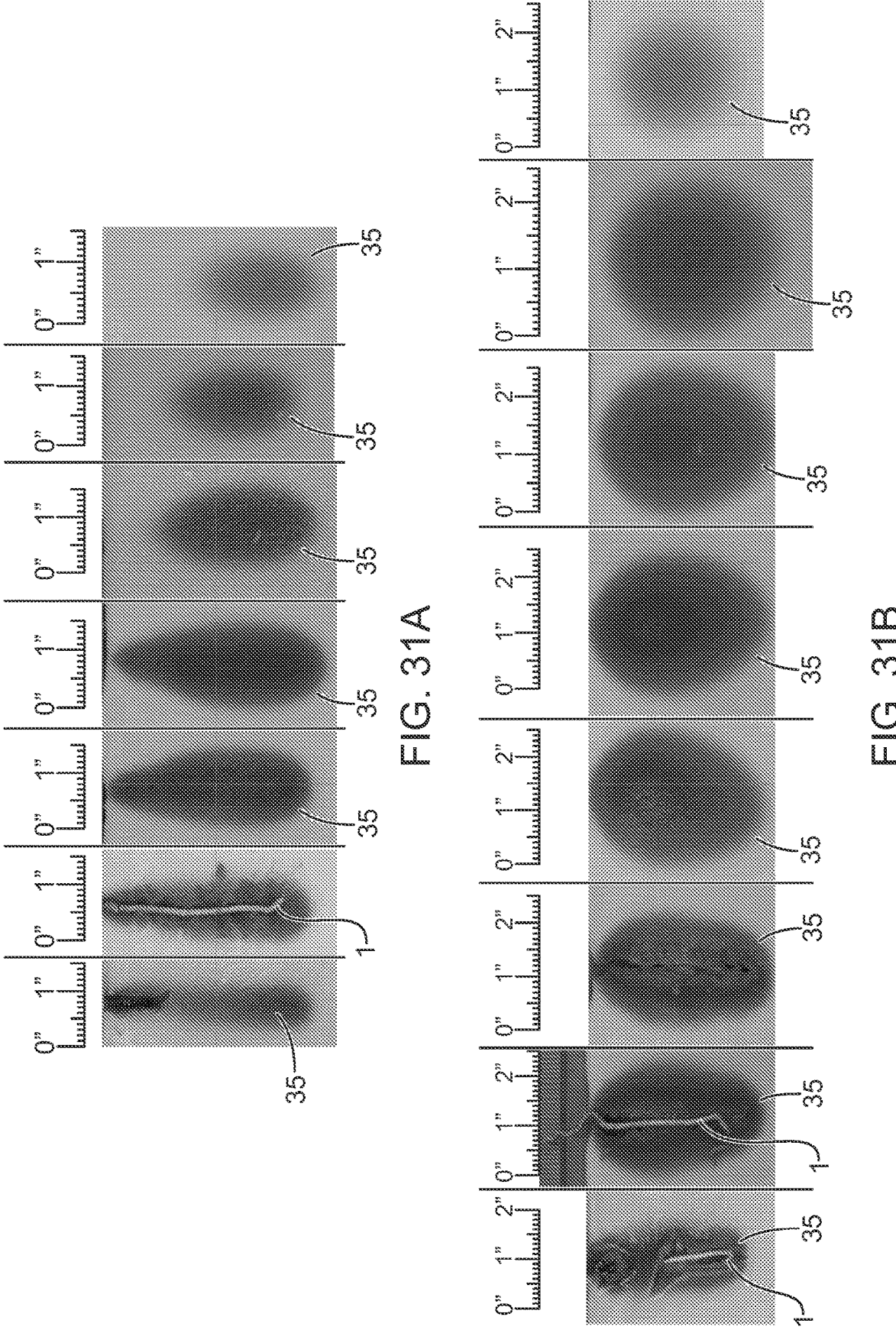
FIG. 31-A shows results from dry RF ablation and FIG. 31-B shows results from wet ablation, both with a helical wire rope structure device.

FIG. 31-A shows results from dry RF ablation, and FIG. 31-B shows results from wet RF ablation, as described.

The helical wire rope structure 1 is configured to form a cavity through physical means (cannula insertion to target) or use of hydro dissection, followed by delivery (injection) of a helical wire rope structure through inserted cannula into the cavity, followed by delivery (injection) of a conductive fluid to the site of ablation through the same or a separate cannula.

Figure 32:
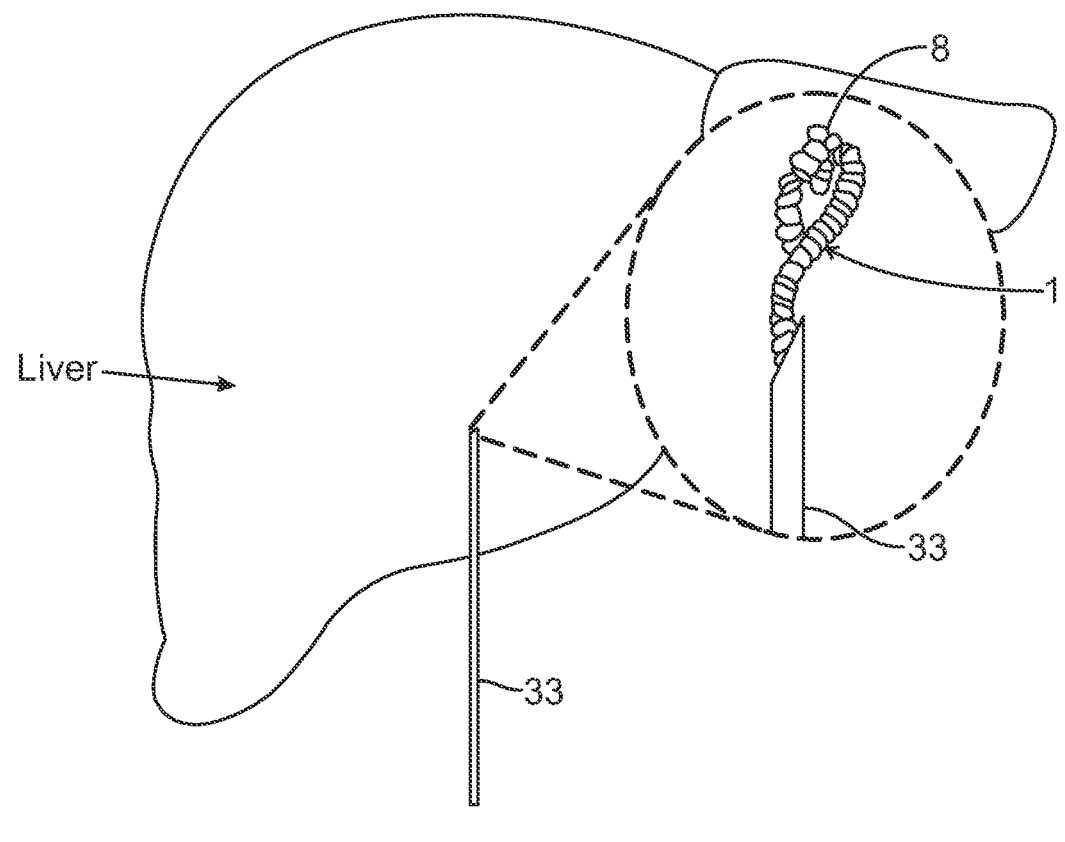
FIG. 32 is a diagram of delivery of a helical wire rope structure into a liver through a beveled needle injector.

FIG. 32 is a diagram of delivery of a helical wire rope structure 1 into the liver through a beveled needle injector, where the end has formed a bunching anchor 8.

One embodiment of the method herein of acute (hyperthermia) ablation utilizing a helical wire rope structure includes percutaneous delivery/deployment through a flexible delivery device using a flexible conductive plunger or device to which the proximal helical wire rope structure is attached as in FIG. 32, and subsequent application of a current to the treatment site with said device, receiving an impedance measurement between the treatment site and a distal return device, and adjusting the flow rate of the irrigant based on the impedance measurement. For example, a high impedance measurement or sudden change in impedance may cause tissue desiccation around the active device, and the fluid rate may be adjusted to increase conductivity at the site of ablation. Upon completing ablation for an acute procedure, the plunger or device mechanism may be retracted to remove the helical wire rope structure prior to closure.

In an embodiment, the system enhances acute helical wire rope structure ablation by irrigating said porous helical wire rope structure using a conductive fluid (e.g., saline, or other electrically conductive fluids into cavity formed during placement, % hypertonicity) pushed at (constant or intermittent) rate through an open-tip interfacing needle or irrigation catheter to generate and maintain comparatively (to state of art, or to a ctrl comparison/interfacing needle) larger ablation (RF HT) volumes. In another embodiment, the system enhances repeated helical wire rope structure ablations by irrigating the porous structure using a conductive fluid (e.g., saline, or other electrically conductive fluids into surrounding tissue, % hypertonicity) pushed at (constant or intermittent) rate to generate and maintain comparatively (to state of art, or to a ctrl comparison/interfacing needle) larger ablation (RF HT) volumes. In yet another embodiment, the system enhances direct current (electrolytic) ablation efficacy by irrigating a helical wire rope structure using a conductive fluid (e.g., saline, or other electrically conductive fluids into surrounding space, % hypertonicity) pushed at (constant vs. intermittent—pros cons) rate. The rate of electrolytically induced necrosis increases due to the helical wire rope structure's larger exposed surface areas available for electrolysis. The inclusion of conductive fluids irrigating the treatment site lowers resistances in target regions, maximizing potential charge delivered over time. A constant "refreshing" of new species directly surrounding a high surface area device serves to increase volume electrochemically ablated by increased species diffusion rate from the site of electrolysis (in particular, acidic species from anode).

In an embodiment, the rate of chemical reaction at the device is a charge transfer rate device-electrolyte.

In an embodiment, the rate of reactant provision and product removal is the mass transfer rate of diffusion and/or migration.

Demonstrated in Table One is RF ablation performed "dry" with a helical wire rope structure injected linearly into a temperature-sensitive tissue mimicking phantom, without the addition of an irrigant, i.e., a perfusate, compared to an ablation performed "wet" by injection of a constant flow hypertonic saline solution over the same amount of time, at the same applied power. Multiple temperature, current, and impedance measurements were recorded over the course of the ablation. An irrigated device maintained more consistent impedance over the experiment duration compared to a dry device. An irrigated device delivered more charge to tissue over the experiment duration compared to a dry device. An irrigated helical wire rope structure maintained a more consistent high temperature compared to a dry device. RF ablation through an irrigated helical wire rope structure resulted in 2.8× expanded ablative volume compared to RF ablation through a dry helical wire rope structure, with measurements taken using Image. The data shown in Table One is from ablation performed with a 3-cm active length helical wire rope structure device (1.2 mm outer diameter) is subjected to 10 W for 2.5 minutes, then 20 W for 2.5 minutes, then 30 W for 2.5 minutes, then 40 W for 2.5 minutes for a 10 minute ablation. Irrigant used in "Wet" RF ablation is a 6% hypertonic saline solution. Initial temperature is the passive temperature of the tissue mimicking phantom prior to RF ablation application, measured using a standard 30-gauge thermocouple. Maximum temperature is the largest temperature recorded over the course of the RF ablation experiment, recorded using a standard 30 gauge thermocouple. Maximum current is the largest current recorded through the system controller. Initial (sustained) impedance is the average impedance recorded over the first 2.5 minutes of applied (10 W) RF ablation. Final (sustained) impedance is the average impedance recorded over the final 2.5 minutes of applied (40 W) RF ablation. Final ablated volume is calculated using the equation for an ellipsoid's volume ($4/3\pi*a*b*c$), where a, b, and c are x, y, and z axis radii of the ablated volume. The final ablation volume for the wet RF ablation is almost 3× versus dry.

TABLE 1

|  | "Dry" RF ablation | "Wet" RF ablation |
|---|---|---|
| Initial Temperature (° C.) | 22.5 | 21.0 |
| Max Temperature (° C.) | 93.5 | 88.3 |
| Maximum Current (Amps) | 0.78 | 1.12 |
| Initial (sustained) Impedance (ohms) | 30 | 30 |
| Final (sustained) Impedance (ohms) | 144 | 30 |
| Final Ablated Volume (cm^3) | 4.36 | 12.17 |

Table Two shows data from an ablation performed with a 2-cm active length helical wire rope structure (1.2 mm outer diameter) subjected to 10 W for 2.5 minutes, then 20 W for 2.5 minutes, then 30 W for 2.5 minutes, then 40 W for 2.5 minutes for a 10 minute ablation. Irrigant used in "Wet" RF ablation is a 6% hypertonic saline solution. Rate of temperature change (dT) is the initial temperature at the start of the newly applied power, subtracted from the final temperature recorded at the end of power application, measured using a standard thermocouple. Maximum current is the largest current recorded through the system controller over the duration at the constant power supplied. Impedance (Z0) is the average impedance recorded over the 2.5 minute RF ablation cycle. Cutoff frequency is the number of power cutoffs (occurring due to recording impedances over 1 kohm) recorded during the 10 minute experiment. Final ablated volume is calculated using the equation for an ellipsoid's volume ($4/3\pi*a*b*c$), where a, b, and c are x, y, and z axis radii of the ablated volume. The final ablation volume of wet exceeds the volume of dry by 2.5×.

TABLE TWO

| dT [10 W, 20 W, 30 W, 40 W] (Tf – T0) / (t = 2.5 min) (C / min) | Z0 [10 W, 20 W, 30 W, 40 W] (ohms) | Imax [10 W, 20 W, 30 W, 40 W] (A) | Cutoff Freq (per 10 min) | Final Ablation Volume (cm^3) |
|---|---|---|---|---|
| 0 mL/min | [3.12, 3.44, 6.12, 6.16] | [30, 28, 35, 190] | [0.57, 0.86, 0.96, 0.50] | 0.6 | 2.78 |
| 1 mL/min | [1.4, 2.8, 3.72, 3.08] | [40, 37, 36, 72] | [0.55, 0.81, 1.04, 1.14] | 0.1 | 5.28 |
| 2 mL/min | [2.0, 3.64, 4.0, 3.6] | [44, 37, 32, 28] | [0.61, 0.74, 1.04, 1.18] | 0.0 | 13.80 |

Figures 33A, 33B, 33C:
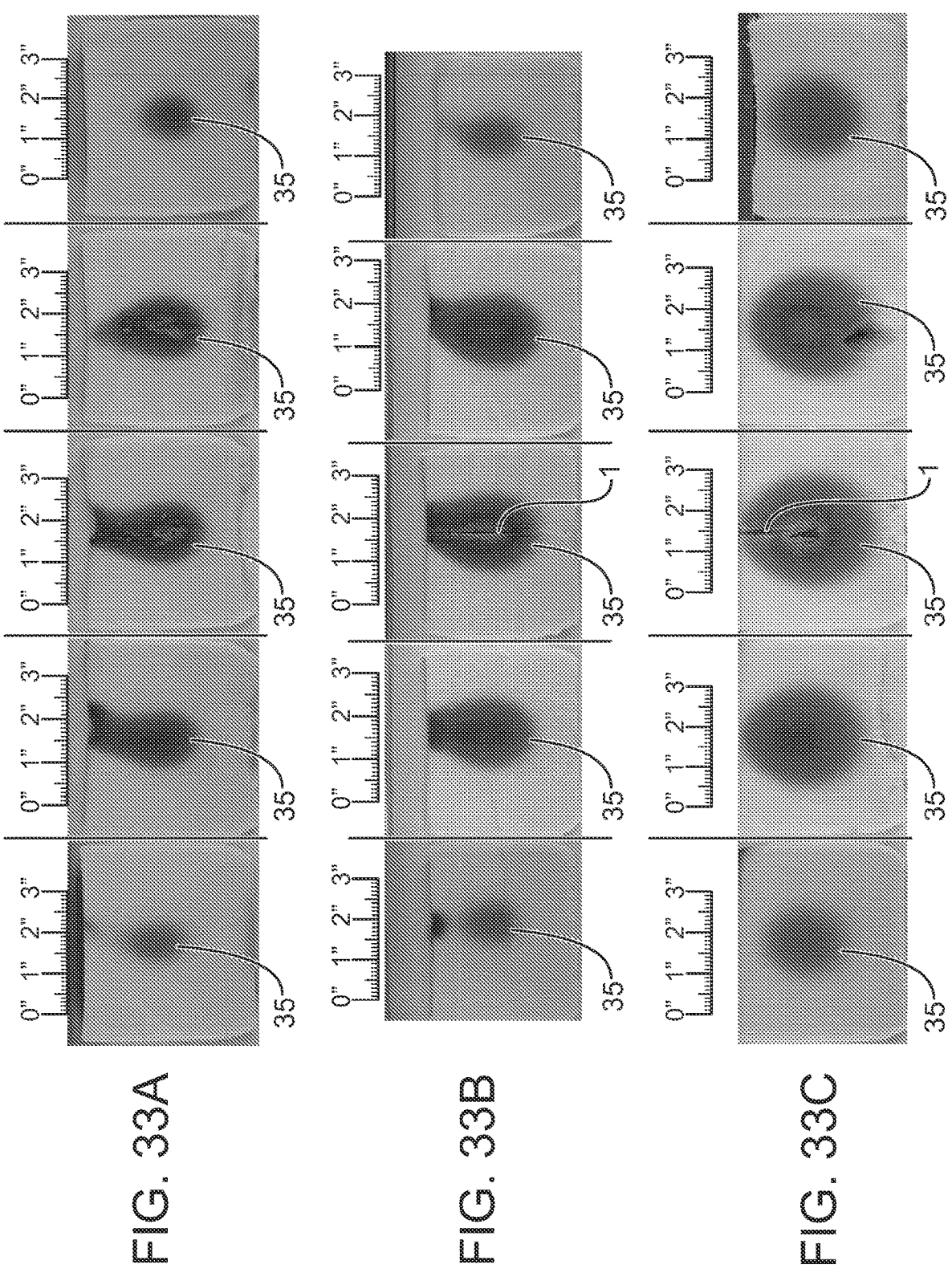
FIGS. 33A-C are images showing the effect of a helical wire rope structure with adjusted flow rate on injection-site temperatures, size and shape of RF ablation progression over a ten minute heating cycle.

FIG. 33A-C are images showing the effect of adjusted flow rate on injection-site temperatures, size, and shape of RF ablation progression over a ten minute heating cycle. A "dry" ablation without irrigant as in 33-A generates intense heat over shorter times at smaller distances radial from the surface of the helical wire rope structure device compared to 33-B and 33-C, and a dry ablation is better suited for minimal, highly targeted ablations. Perfused helical wire rope structures achieve a more controlled temperature rise (smaller dT) and more consistent impedance (R0) over the heating cycle, achieve higher currents at similarly applied powers, and are better suited for producing larger ablation volumes. Note that the ablation volumes are greater in 33-C, having a larger volume of irrigant of 2 mL, than in 33-B with irrigant of 1 mL.

Figure 34:
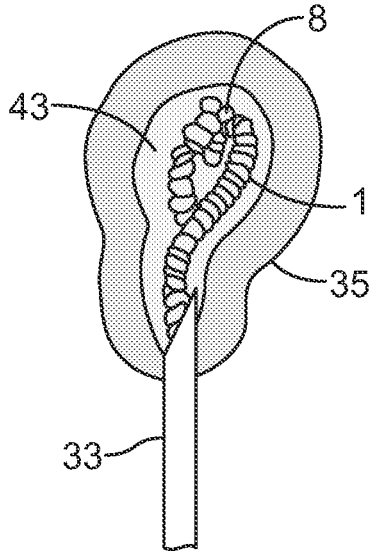
FIG. 34 is a diagram showing delivery of an irrigant into tissue through the same needle injector as in FIG. 33, showing fluid able to pass through breaks or turns in the coils and along the length of the helical wire rope structure.

FIG. 34 is a diagram showing delivery of a perfusate into tissue through the same needle injector, whereby fluid is able to pass through breaks (turns) in the coil and along the length of the multi-stranded device.

Figure 35:
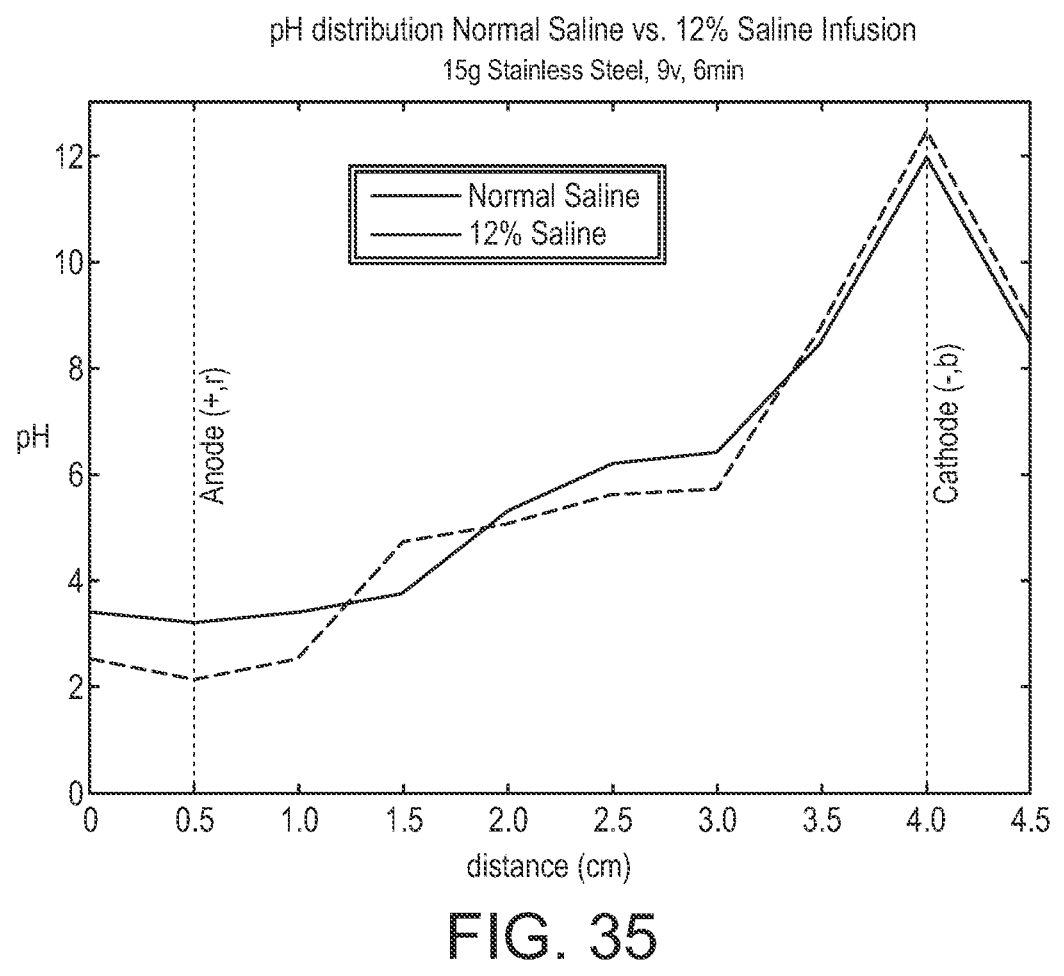

Plotted in FIG. 35 is data from an experiment studying electrolytic ablation performed in a normo-ionic environment through stainless steel needle devices placed into a pH-sensitive tissue mimicking phantom compared to an electrolytic ablation performed in a hyper-ionic environment over the same time, 10 minutes, at the same volume, 9V. Multiple pH measurements were recorded one minute after the applied DC was stopped. An helical wire rope structure in a more hyper-ionic environment produced marginally more extreme pHs (lower at the anode, higher at the cathode) relative to the normo-ionic counterpart, with pH measurements recorded using a standard 30 g micro-pH probe (Thermo-Fisher).

FIG. 35 is a plot of pH distribution over space in a pH sensitive phantom comparing normal and hyper-ionic environments (simulating injection of hyper-conductive perfusate).

Figure 36:
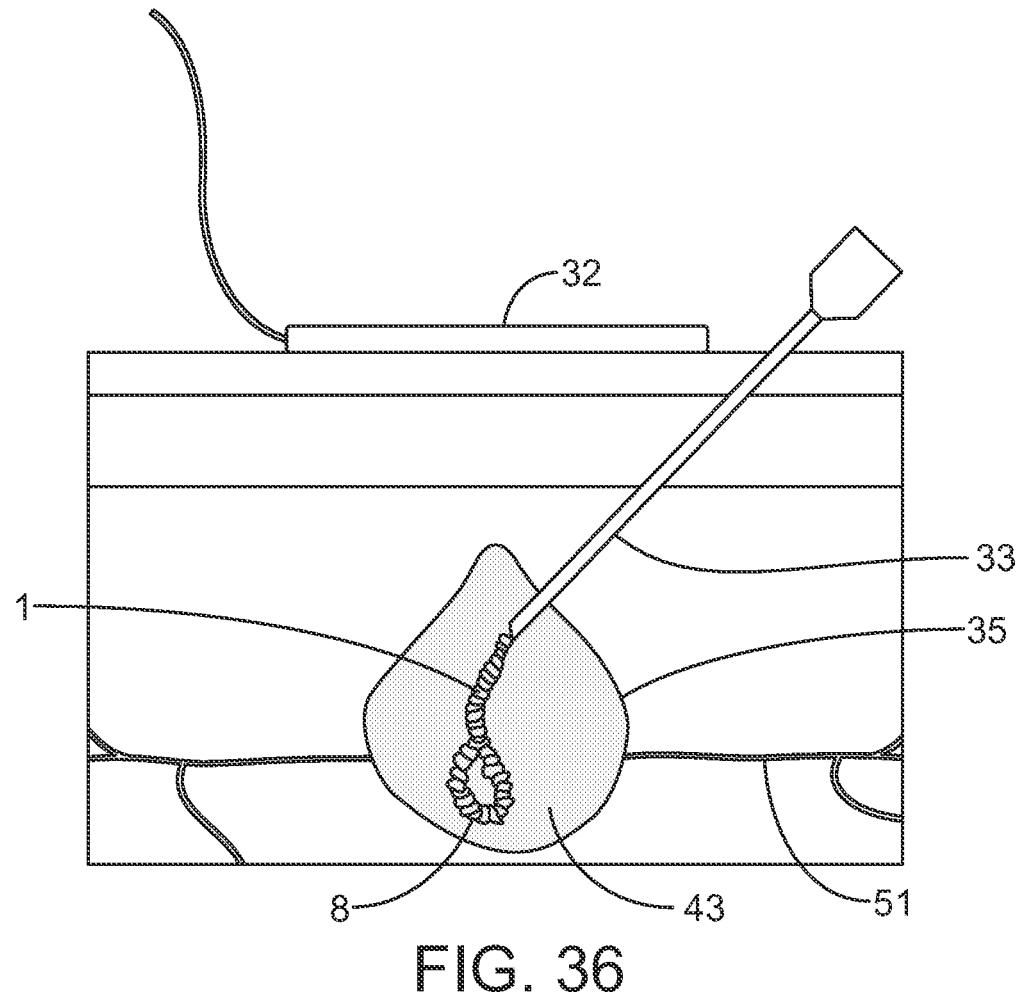
FIG. 36 is a diagram showing interfacing and applied DC between a helical wire rope structure device and a surface patch electrode.

FIG. 36 is a diagram showing interfacing by a needle-type DC device with an ablation pattern 35 shown from a helical wire rope structure device 1 on a target nerve 51 and a surface patch device, or TENS unit 32. A negative potential is provided by the DC device and the TENS 32 provides a positive return. One device is positive and the other negative.

Figure 37:
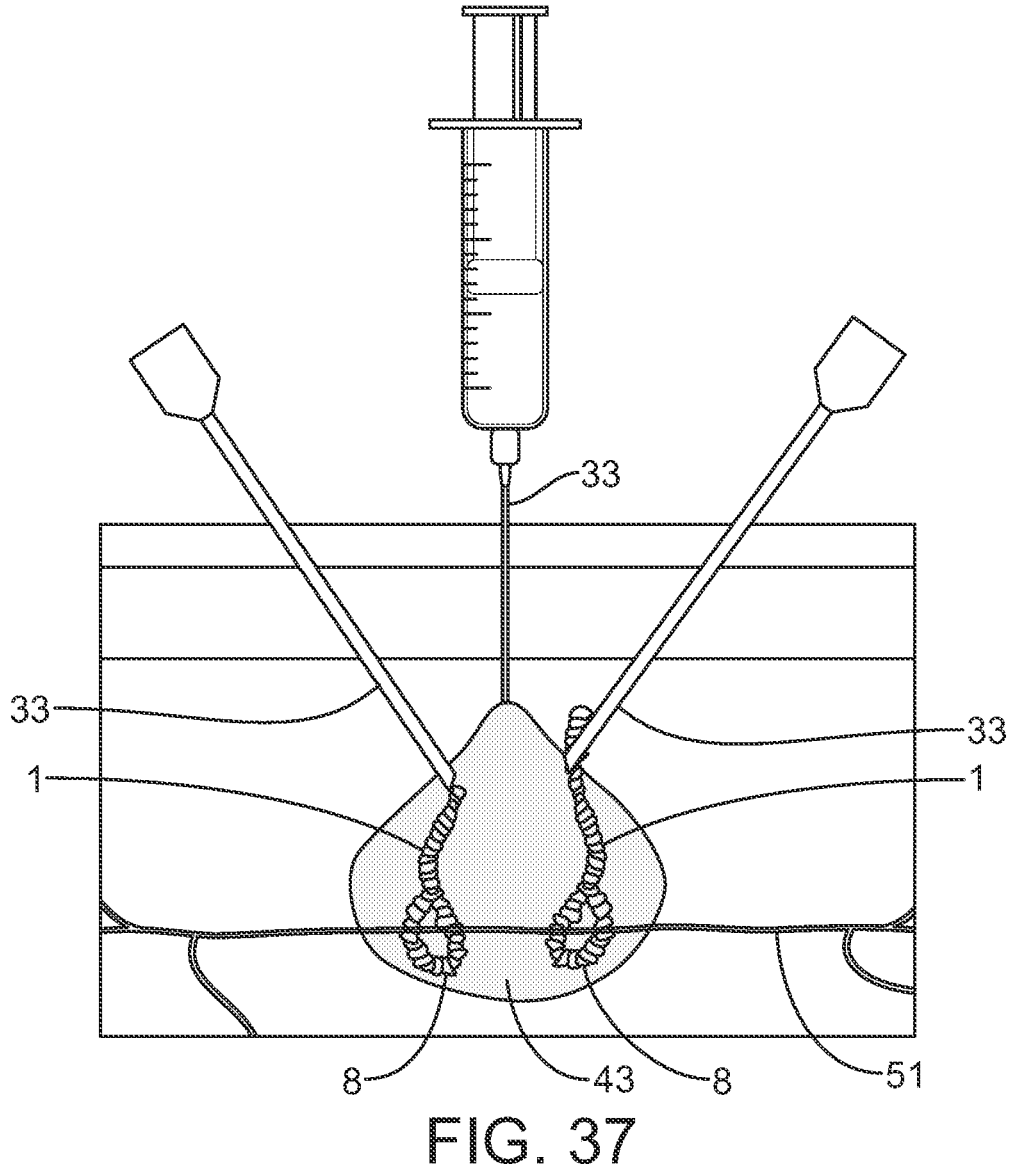
FIG. 37 is a diagram showing interfacing and applied DC between two helical wire rope structures adjacent to a target nerve, with irrigant spread around both.

FIG. 37 is a diagram depicting interfacing and applied DC devices with an ablation pattern 35 shown from two helical wire rope structure devices 1 with irregular shape/anchors 8 adjacent to the target nerve 51.

In an embodiment, the method is configured to direct current (electrolytic) efficacy and reducing treatment time through sequential irrigation→EA irrigation→RF ablation using helical wire rope structure, as shown in the block diagram which is FIG. 38.

In an embodiment, the method is configured to enhance RFA efficacy and reduces treatment time through a method of treatment shown in the block diagram which is FIG. 39.

Preservation of non-targeted tissue remains a challenge for thermal and electrochemical ablation. A method of ablation herein concerns the use of coatings 19 distributed along the length of the helical wire rope structure to affect the distribution of an applied treatment. In one configuration, these coatings 19 may be insulative, as demonstrated in FIGS. 40-A and 40-B, whereby an insulative heat-shrink polymer coats the helical wire rope structure 1 intermittently and creates ablation patterns 35 (thermal or electrochemical) at the noncoated areas 6 while maintaining tissue integrity near coated sections, which are high impedance and not exposed to ionic environments.

Figure 41:
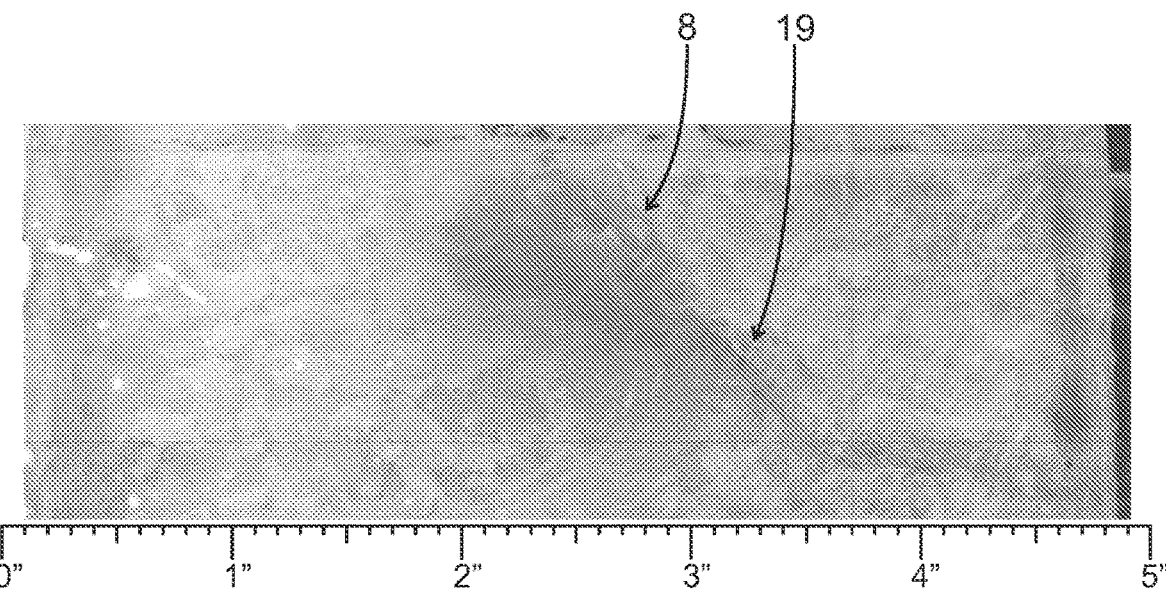
FIG. 41 is an image of a helical wire rope structure in a tissue gel with an exposed distal tip/bunching anchor with other sections having a coating to prevent ablation in the area with the coating.

FIG. 41 demonstrates a use case through which a clinician injects a partially coated helical wire rope structure with an exposed distal tip/bunching anchor 8 as well as an exposed proximal collector, which may be interfaced with percutaneously upon initial placement for treatment, placed subcu-
taneously after treatment, and re-interfaced with through
percutaneous means at later time points. Of significance are
the sections with coating 19 which allow the selective
ablation of tissue near the active distal tip 8 with minimal
residual heating along the coated length of the electrode.
That is, by intentionally selecting a pattern of coating and
noncoating, a single wire structure device can ablate two or
more separate sites, i.e., centimeters apart.

Figure 42:
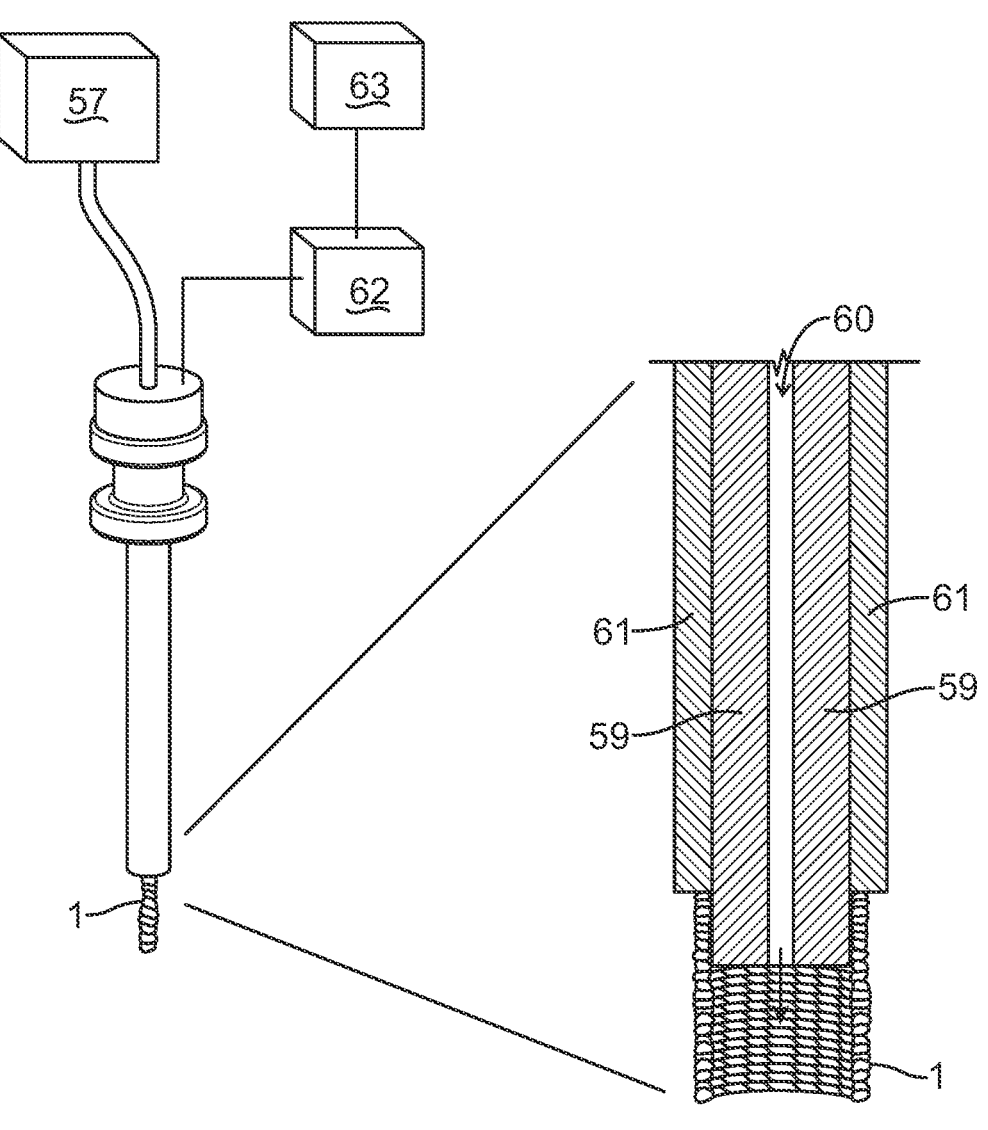
FIG. 42 is a diagram of one embodiment of a system for acute ablation with a helical wire rope structure enabled for irrigation.

FIG. 42 is one embodiment of an acute ablation system 56
with a helical wire rope structure electrode configured with
irrigation. A micro-infusion pump 57 provides irrigant
through a line 58 to the plunger 59 which contains an inner
channel 60 for flow of irrigant through it. The plunger is in
a cannula 61. At the distal end of the plunger one end of a
helical wire rope structure is mechanically coupled by
gluing or welding (or other similar means) and the other end
of the helical wire rope structure extends beyond the distal
end of the plunger. A controller 62 is connected to a
generator 63 (RF/DC) and the controller is also connected to
the plunger which maintains an electrical connection with
the helical wire rope structure. Irrigant flows through the line
and into the inner channel whose distal end is at the distal
end of the plunger. Sensors for temperature and pH are
optionally embedded in the distal end of the plunger. The
cannula and plunger are perspective views, the pump, con-
troller and generator are block diagrams, and the close up is
a section view.

Additional Methods of Treatment

RF, MW or HIFU are sources of clinical hyperthermic
ablation, generating temperatures in excess of about 60
degrees Celsius. Aside from HIFU, these energies are
applied from a generator connected to needle-like applica-
tors inserted into or surrounding the tumor. Typical lesions
generated may be modeled as three-dimensional spheroids,
with the major axis of the lesion aligned parallel to the
applicator shaft, and two minor axes of the lesion lying
perpendicular to the shaft. Though the lesion's major axis
may be controlled by selecting different lengths of uninsu-
lated applicator tips, necrosing along the minor axis is more
cumbersome. Attempts to overcome this limitation have
involved increasing the probe gauge, using several applica-
tors in combination or multiple probes per applicator, and
the use of expandable applicators.

Helical wire rope structure and non-helical wire structures
can be utilized for fiducial marking of a tumor, follow up and
tracking of the site of tumor and treatment area. Multi-
functional long-term retention provides ability to treat, mark
and re-treat without additional injection or skin puncture.
That is, the originally injected wire structure device can
remain in the tissue, providing the clinician the option of
additional ablation follow up procedures, commonly or
re-ablations, without the re-insertion of a large diameter
conventional probe, but instead a thin probe may be used
that connects to the large surface area of the wire structure
device. In this sense, ablation with the wire structure device
offers: 1) repeatable procedures with thin (needle) energy
conductive probe, (2) much larger surface area and (3)
customizable shape. Because wire structure devices can
integrate into the tissue and dwell for extended periods, they
open several long-term treatment possibilities; re-treatment,
in cases when a tumor returns after initial acute ablation,
without additional injection or skin puncture; re-treatment
using energy coupling; and ongoing treatment with continu-
ous stimulation; and chronic enhancement of drug uptake of
oral, IV, intra-arterial chemotherapy agents. Additionally,
one or more classes of tumors may carry a known risk of recurrence. With the current state of the art, the recurrence
may be re-treated carrying similar and/or greater procedural
and/or surgical risks if it is even possible to re-intervene. The
wire structure devices address this difficulty. Because the
wire structure devices can remain chronically in situ, they
can be used as a fiducial marker for precise re-evaluation of
the target site as well as repeated treatments to address
recurrent tumor growth. This greatly reduces the time,
trauma and cost of repeated ablative insertions and/or resec-
tion procedures.

The device enables tissue ablation of multiple shapes,
adaptable to specific anatomy of a tumor and its surrounding
vasculature or other structures (i.e. gallbladder, porta hepa-
tis, bile ducts).

Tumors in complicated locations may be treated by
deploying a helical wire rope structure in a (partial or
complete) half-moon shape, or any other complex shape
which a skillful clinician can devise by manipulation of the
delivery device. Examples of such tumors are carcinoma on
the outside of—or surrounding of—an organ, a blood vessel,
or in a volume that itself is more of a shape of a half-moon
than a round sphere.

A generated coagulation zone in RF ablation is strongly
limited by heat sinks—fluid (e.g., blood) flow through
vessels near a tumor causes local pockets of convective
heating such that RF ablation is unable to achieve consistent
necrosis near the tumor. For example, in the case of HCC,
traditionally risky locations for treatment are tumors
attached to vasculature (perivascular) which are adjacent to
extrahepatic vital organs or larger intrahepatic vessels,
which can alter the size of the ablation zone due to the
heat-sink effect, resulting in aggressive recurrences after
ablation. Intravascular tumor spread along the peritumoral
portal vein contributes greatly to HCC recurrence and
spread. The helical wire rope structure is capable of sur-
rounding vasculature closely and in a user-customized man-
ner. Delivery of the helical wire rope structure may be in
parallel alignment with the vasculature or hooked around the
vasculature in a C or J-shape. Deploying the helical wire
rope structure circumferentially (helically) around the vessel
allows regions of focal RF ablation heat deposition around
a perivascular tumor, allowing for ablation around corners.

Coagulation zones in RF ablation are also strongly limited
by roll-off, the cessation of RF power due to sudden increase
in electrical impedance with the active device surrounded by
desiccated tissue, which has an insulation effect. Ablation
with saline infusion through cannula may limit coagulation
on the device surface. Pulsing with RF at regular intervals,
and ramping power from low wattages to mid-level power
settings may help avoid charring as a result of rapid power
delivery at the wire structure surface The primary goal is to impair the target tissue: in the case
of malignant tumors, permanent destruction, but in the case
of peripheral nerves, temporary impairment of neural con-
duction for applications such as pain relief (sensory block,
afferent nerve fiber block), reduction of spasticity (motor
fiber block, efferent nerve fiber block), or modulating the
autonomic function of an organ, organ system or an indi-
vidual (autonomic nerve block affecting either autonomic
afferents or efferent). In the case of cancer, the goal is
elimination of viable malignant (cancerous) cells in a des-
ignated tumor volume and to provide immediate pain relief
by affecting the afferent innervation into cancerous tissues.
As such, ablation is intended to include a 0.3 cm to 1 cm
ablative margin of non-malignant tissue, in order to mini-
mize the chance of local tumor progression or recurrence.
Known risk factors of tumor recurrence post-ablation include an insufficient ablative margin, the presence of vasculature (e.g., as in HCC) with the odds of tumor recurrence highly correlated with larger, irregular tumors. Larger tumors, typically defined as tumors over about 3 cm in diameter, may utilize multiple overlapping probes, applied in succession or simultaneously, to facilitate an ablative margin.

It is also desirable for ablation to be highly precise to preserve as much normal tissue as possible. In HCC, functional hepatic reserve is a primary predictor for long-term patient survival. Well-planned ablative therapies serve to minimize damage to surrounding cirrhotic parenchyma. Preservation of nephrons in the context of renal cell carcinomas, or epithelial cells of the lung in the context of adenocarcinomas may facilitate positive patient outcomes. The ability to preserve structures surrounding a tumor remains a challenge for ablation modalities.

One or more helical wire rope structures may be injected centrally within the tumor site, or at multiple oblique sites tangential or adjacent to the targeted tumor to create different polar arrangements for selective heating or application of an electric field across wire devices. Once placed, the helical wire rope structure is intended to reside within the tissue. High contrast/radiopacity exhibited by the helical wire rope structure enables accurate localization of the tumor and previous treatment area under computed tomography or fluoroscopy. Re-interfacing and retreatment through the helical wire rope structure can be accomplished through electrical coupling with an external energy source, and subsequent hyperthermal or non-thermal modes of ablation.

Percutaneous ablation is a well described method for minimally invasive treatment of a variety of conditions, both malignant and non-malignant in nature. Common practice may implement precision guidance of a ridged probe to a specific location using medical imaging (ultrasound, CT, MRI or Fluorography). Successful treatment for safe, accurate placement of the probe may not be possible due to geometric and anatomic constraints such that safe positioning and adequate tumor coverage cannot be achieved. The properties of the helical wire rope structure allow for greater flexibility in achieving successful placement as well as geometric path and contouring of tumor coverage heretofore not possible.

Table Three The devices described herein are configured for ablation of malignant tumors as follows:

| Primary | Metastatic |
| --- | --- |
| Hepatocellular Carcinoma (primary liver tumor) | Liver |
| Renal Cell Carcinoma | Lung |
| Lung Carcinoma | Bone |
| Pancreatic Cancer | Lymph Nodes |
| Thyroid | Adrenal Gland |
| Breast | Brain |
| Colorectal | Superficial and deep soft tissues (for example retroperitoneum) |
| Adrenal Gland | |

If metastasis are solitary or few in number, they may be candidates for percutaneous ablation with the actual technique dependent on location, size, vascular or neural involvement. Because metastatic disease may occur with many cancers and because target organs for involvement are frequently suitable for percutaneous ablation, the matrix for potential treatment grows large, particularly in the liver, lung and soft tissues.

Some tumors or growths do no behave in a malignant fashion, but produce pain or dysfunction, nonetheless. An example is an osteoid osteoma of bone which may be quite painful and responds to relatively low power RF ablation successfully. Uterine fibromas represent another case, similarly non-malignant but treatable by ablation methods. These and other lesions would are treatable with ablation by the wire structure devices herein.

Broadly, percutaneous ablation methods fall into thermal, non-thermal and electroporation categories with radiofrequency (RF), microwave (MW) and irreversible electroporation (IRE). Specific energy specifications may depend on the method used and affects the volume of treatment, i.e., the size of the tumor to be ablated. Treatment volume may be summed or stacked through the simultaneous use of multiple probes, or sequential repositioning of a single probe, many of which may increase cost, time and complexity. This, in turn, increases the potential for adverse events and complications.

In general, volumetric ablation zones (ABZ) are affected by deposited power in watts and duration of application in minutes. Example ranges for thermal ablations include: RFA—10 to 45 W for 2 to 10 minutes and MW—40 to 140 W for 2 to 6 minutes.

Because IRE uses a non thermal profile through the use of short bursts of high voltage, high current volumetrically constrained in a defined multi-pattern bipolar fashion, the power and endpoints are treated differently.

Diameter and resultant volume of ablation are estimated through the use of time/power/volume charts generated through testing in physiologic and animal models. Observational feedback at the time of treatment is also used to determine the treatment endpoint. The limits of actual size depend on the location, organ and anatomy, but may fall into a range of about 1 cm to about 4 cm. The ability to place the wire structure devices herein more precisely and to create a geometric conformal active region allows for more complex and larger ablation zones.

In addition to the foregoing, some embodiments may include additional aspects as follows.

A method of treating a tissue target in a body comprising the steps of implanting a wire structure device in, on or near the tissue target, said wire structure device being biocompatible and capable of chronic implantation in said body, providing grounding means exterior to said body, contacting the wire structure device through a percutaneous probe, said probe being energy conductive, and delivering energy through said probe to said tissue target, said energy being configured to lesion or destroy said tissue target, and withdrawing the probe from the body. In another embodiment the method further comprises at the end a step of imaging the wire structure device as implanted as a fiducial marker and then repeating one or more steps after implanting the wire structure device. When the tissue target is a peripheral nerve, one embodiment of the method is a new step after imaging of gradually ramping up direct current to the peripheral nerve from, e.g., zero mA to 0.1 mA in less than 30 seconds, and thereafter increasing gradually to prevent pain with patient feedback or other means of achieving pain block. In ablation, lidocaine is often injected at the ablation location prior to applying ablation. With the implanted helical wire rope structure device which is implanted prior to the ablation procedure, instead of lidocaine injection the clinician may pre-treat with slowly ramped DC to block the sensory innervation of the tissue prior to EA ablation or RF ablation.

Using the same method, the wire structure comprises a helical wire rope structure or a non-helical wire rope structure, the latter being selected from the group consisting of rolled, folded, extruded and the like. The energy delivered through the probe may be selected from the group of radiofrequency current, microwave energy, direct current and changing magnetic field inducing alternating currents, and is sufficient to heat said tissue target to at least 60 degrees C. In another embodiment said energy delivered through the probe is direct current and is sufficient to lesion said target tissue through an induced pH 4 or less or 10 or more. In yet another embodiment of the method, energy delivered to the probe is current and produces reversible electroporation, irreversible electroporation or electrolytic lesioning.

In yet another aspect, the amplitude of the direct current to achieve the lasting pH change is reached by initially slowly ramping the DC from zero mA to 0.1 mA in less than 10 seconds, thereafter increasing the slow rate as applicable such that the patient does not report sensation of DC applications to avoid the use of pharmacological anesthetic agents consisting of lidocaine, marcaine, or similar as the means of reducing pain during the application of DC to block pain perception while applying treatment to the tissue.

In an embodiment, the system is configured to treat a neurological condition comprising an implantable folded wire structure intended to be left in place chronically that can fold up or bunch up or fold in when brought in mechanical contact with the biological target tissue or surrounding tissues, an percutaneous interfacing device intended for the temporary penetration of skin to conduct energy from outside of the body to the implanted folded wire structure inside the body, the interfacing device having a skin penetrating insulated portion and an uninsulated portion, both portions intended to penetrate the skin, the insulated portion penetrating the outer layers of the skin and the uninsulated portion intended to interface with the chronically placed folded wire structure, a connector to an energy signal generation device, and a signal generation device providing the energy, and the signal generation device providing the energy being a radiofrequency generator, a microwave generator, a direct current generator. In another embodiment of the system, the signal generation device providing the energy being a direct current and a radiofrequency generator, the device being capable to first generate a ramped direct current to sensory block neural tissue in the vicinity of the implanted folded wire structure device, and second being able to provide a radiofrequency energy to ablate target tissue in the vicinity of the implanted folded wire structure device.

In an embodiment, the method is configured for treating cancerous tissue by applying an electrical energy signal to cancerous tissue with the aid of a chronically implanted folded wire structure in close timed proximity to the application of chemotherapy agents to a cancer patient, the treatment consisting of multiple applications of either treating cancerous tissue with RF, MW, or DC energy alone, or treating cancerous tissue with RF, MW, or DC energy in close time proximity with therapeutic agents such as chemotherapeutic drugs.

In an embodiment, the method is configured for the implanted folded wire structure to facilitate repeat treatment via RF, MW or DC energy that is being delivered by a 24 gauge or smaller needle, allowing for a patient-friendly repeat treatment.

We claim:
1. A method of ablation of a tissue target in a body comprising the steps of:
   implanting an ablation electrode comprising:
      a percutaneous element; and
      a wire structure mechanically attached to said percutaneous element and in communication with a tissue target, said wire structure being biocompatible and forming an irrigation channel, said wire structure being formed of multiple strands that are deformed by mechanical compliance upon implantation so as to bunch relative to the tissue target when implanted, said wire structure being formed as a helical wire rope structure;
   delivering an irrigant in, on or near said tissue target through said irrigation channel of said wire structure;
   grounding the device to implement a flow of electrical current between the device and a grounding pad;
   delivering energy through said percutaneous element to said wire structure creating heat at said tissue target, said heat being configured to lesion or destroy at least a portion of said tissue target; and
   withdrawing said percutaneous probe and said ablation electrode from the body.

2. The method of claim 1, wherein said step of delivering an irrigant in, on or near said tissue target through said wire structure is, at least partially, performed while performing said step of delivering energy.

3. The method of claim 1 wherein said helical wire rope structure is formed from a primary coil of parallel strands of wire which comprise a continuous unbroken strand.

4. The method of claim 1 wherein said energy is selected from the group consisting of radio frequency current, microwave energy, and changing magnetic field inducing alternating currents.

5. The method of claim 1 wherein said energy is configured to heat said tissue target to at least 60 degrees C.

6. The method of claim 1 wherein said step of withdrawing said percutaneous element from the body is performed within the same day as said step of delivering energy.

7. The method of claim 1 wherein said ablation electrode includes a temperature sensor.

8. The method of claim 1 wherein said wire structure is formed of multiple strands measuring within the range of 2 to 300 microns diameter.

9. The method of claim 1 further comprising the steps of:
   after said step of delivering energy, repositioning said ablation electrode; and
   repeating said step of delivering energy.

10. A method of ablation of a tissue target in a body comprising the steps of:
   implanting a device comprising:
      a wire structure in communication with, on or near a tissue target, said wire structure being biocompatible and forming an irrigation channel, said wire structure being formed of multiple strands that are deformed by mechanical compliance upon implantation so as to bunch relative to the tissue target when implanted, said wire structure being formed as a helical wire rope structure;
   grounding the device to implement a flow of electrical current between the device and a grounding pad;
   contacting the wire structure through a percutaneous probe, said percutaneous probe being energy conductive;
   delivering energy through said percutaneous probe to said wire structure creating cell damage at said tissue target, said cell damage configured to lesion or destroy at least a portion of said tissue target;

delivering an irrigant in, on or near said tissue target through said irrigation channel while delivering energy through said percutaneous probe; and withdrawing said percutaneous probe from the body.

11. The method of claim 10, wherein said energy is direct current and is configured to lesion at least a portion of said target tissue through an induced pH 4 or less or 10 or more.

12. The method of claim 10, wherein said energy is electric current and produces reversible electroporation, irreversible electroporation or electrolytic lesioning.

13. The method of claim 10 wherein said helical wire rope structure is formed from a primary coil of parallel strands of wire which comprise a continuous unbroken strand.

14. The method of claim 10 wherein said percutaneous probe is mechanically attached to said wire structure and said step of withdrawing said percutaneous probe also withdraws said wire structure.

15. The method of claim 14 wherein said step of withdrawing said percutaneous probe from the body is performed within the same day as said step of delivering energy.

16. The method of claim 10 wherein said device includes a temperature sensor.

17. The method of claim 10 wherein said wire structure is formed of multiple strands measuring within the range of 2 to 300 microns diameter.

18. The method of claim 10 wherein said wire structure is formed so as to have a surface area per unit length of at least 135 mm$^2$/cm.

19. The method of claim 2 wherein said step of delivering an irrigant while performing said step of delivering energy further comprises adjusting the flow rate of the irrigant based on measurement of at least one parameter selected from the group of temperature, pH, and impedance.

20. A method of ablation of a tissue target in a body comprising the steps of:

implanting a device comprising:

a wire structure in communication with, on or near a tissue target, said wire structure being biocompatible and defining an irrigation channel, said wire structure being formed of multiple strands that are deformed by mechanical compliance upon implantation so as to bunch relative to the tissue target when implanted, said wire structure being formed as a structure selected from the group of helical wire rope structures and braided wire rope structures, and said wire structure being formed so as to have a surface area per length of at least per unit length of at least 135 mm$^2$/cm;

grounding the device to implement a flow of electrical current between the device and a grounding pad;

contacting the wire structure through a percutaneous probe, said percutaneous probe being energy conductive;

delivering energy through said percutaneous probe to said wire structure creating cell damage at said tissue target, said cell damage configured to lesion or destroy at least a portion of said tissue target;

delivering an irrigant in, on or near said tissue target through said irrigation channel; and withdrawing said percutaneous probe from the body.

* * * * *